United States Patent [19]

Brady

[11] Patent Number: 5,766,606
[45] Date of Patent: *Jun. 16, 1998

[54] CLONING OF NON-IGA FC BINDING FORMS OF THE GROUP B STREPTOCOCCAL BETA ANTIGENS

[75] Inventor: L. Jeannine Brady, Gainesville, Fla.

[73] Assignee: University of Florida Research Foundation, Inc., Gainesville, Fla.

[*] Notice: The term of this patent shall not extend beyond the expiration date of Pat. No. 5,595,740.

[21] Appl. No.: 714,481

[22] Filed: Sep. 16, 1996

Related U.S. Application Data

[63] Continuation of Ser. No. 242,932, May 16, 1994, Pat. No. 5,595,740.

[51] Int. Cl.$^6$ .......... A61K 39/09; C12N 15/31; C12N 1/21; C07K 14/315
[52] U.S. Cl. .......... 424/244.1; 435/320.1; 435/252.3; 530/350; 536/23.7; 424/190.1
[58] Field of Search .......... 536/23.7; 424/190.1, 424/192.1, 244.1; 435/320.1, 252.3; 935/65, 10; 930/200; 530/350

[56] References Cited

U.S. PATENT DOCUMENTS 5,595,740  1/1997  Brady .................. 424/190.1
5,644,030  7/1997  Faulmann .

OTHER PUBLICATIONS

Anthony, B.F. et al. (1990) "Nonimmune binding of human immunoglobulin A to type II group B streptococcus" Infect. Immun. 58:1789–1795.

Baker, C.J. et al. (1978) "Immunogenicity of polysaccharides from Type II, Grou B streptococci" J. Clin. Invest. 61:1107–1110.

Brady, L.J., M.D.P. Boyle (1989) "Identification of non–immunoglobulin A Fc binding forms and low molecular weight secreted forms of the group B streptococcal beta antigen" Infect. Immun. 57:1573–1581.

Chun, C.S.Y. et al. (1991) "Group B streptococcal C protein–associated antigens: association with neonatal sepsis" J. Infect. Dis. 163:786–791.

Cleat, P.H., K.N. Timmis (1987) "Cloning an expression in *Escherichia coli* of the ibc protein genes of group B streptococci: Binding of human immunoglobulin A to the beta antigen" Infect. Immun. 55:1151–1155.

Fisher, G., R.E. Horton, R. Edelman (1983) "From the National Institute of Allergy and Infectious Diseases: Summary of the National Institutes of Health workshop on group B streptococcal infection" J. Infect. Dis. 148:163–166.

Heden, L.–O, E. Frihz, G. Lindahl (1991) "Molecular characterization of the IgA receptor from group B streptococci: sequence of the gene, identification of a proline–rich region with unique structure and isolation of N–terminal fragments with IgA–binding capacity" Eur. J. Immunol. 21:1481–1490.

Jerlstron, P.G., G.S. Chatwall, K.N. Timmis (1991) "The IgA binding antigen of the C protein complex of group B streptococci: sequence determination of its gene and detection of two binding regions" Mol. Microbiol. 5:843–849.

Lindahl, G., B. Akerstrom, J.–P. Vaerman, L. Stenber (1990) "Characterization of an IgA receptor from group B streptococci: specificity for serum igA" Eur. J. Immunol. 20:2241–2247.

Madoff, L.C. et al. (1992) "Protection of neonatal mice from B streptococcal infection by maternal immunization with beta C protein" Infect. Immun. 60:4989–4994.

Michel, J.L. et al. (1991) "Cloned alpha and beta C protein antigens of group B streptococci elicit protective immunity" Infect. Immun. 59:2023–2028.

Michel, J.L. et al. (1992) "Large identical, Tandem–repeating units in the C protein alpha antigen gene, bca, of group B streptococci" Proc. Natl. Acad. Sci. USA 89:10060–10064.

Russell–Jones, G.J., E.C. Gotschlich (1984) "Identification of protein antigens of group B streptococci with special reference to the Ibc antigens" J. exp. Med. 160:1476–1484.

Russell–Jones, G.J., E.C. Gotschlich, M.S. Blake (1984) "A surface receptor specific for human IgA on group B stepococci processing the Ibc protein antigen" J. Exp. Med. 160:1467–1475.

Kvam, A.I., O.–J. Iverson, L. Bevenger (1991) Binding of human IgA to HCl–extracted C protein from group B streptococcus (GBS): APMIS 100:1129–1132.

Brady, L.J. et al. (1994) "Cloning of Non–Iga Fc Binding Forms of the Group B streptococal Beta Antigen" ASM 4$^{th}$ International Conference on Streptococcal Genetics, May 15–18, Santa Fe, New Mexico, p. 33, abstract T17.

Flores, A.E. et al. (1993) APMIS 101:41–49.

Paul, E.E. (1993) Fundamental Immunology, 3$^{rd}$ Edition, Raven Press, N.Y. pp. 933–935.

Jerlstrom, P.G. et al. Mol. Microbiol., vol. 5, pp. 843–849, 1991.

Brady, L.J. et al. Infect. Immun. vol. 57, pp. 1573–1581, 1989.

Brady, L.J. et al. ASM 4th International Conference on Strepotococcal Genentics, Santa Fe, New Mexico, p. 33, abstract T17, May 1994.

Madoff, L.C. et al. Infect. Immunol. vol. 60, pp. 4989–4994, 1991.

Heden, L.O. et al. Eur. J. Immunol., vol. 21, pp. 1481–1490, 1991.

Paul, W.E. Fundamental Immunology, 3rd Ed. Raven Press, N.Y., pp. 933–935, 1993.

*Primary Examiner*—Mary E. Mosher
*Attorney, Agent, or Firm*—Saliwanchik, Lloyd & Saliwanchik

[57] ABSTRACT

The subject invention concerns the genetic manipulation of the gene encoding a group B streptococcal (GBS) surface protein known as the beta antigen. The beta antigen is known to bind to the Fc region of IgA immunoglobulins in a non-immune manner. The portion of beta antigen gene which encodes the IgA binding function has been identified and removed using genetic engineering techniques. The novel polypeptide encoded by the altered beta antigen gene does not bind to IgA but does immunoreact with monospecific anti-beta antigen antisera raised against the wild-type beta antigen protein. This non-IgA binding form of the beta antigen may be used as a component in a human vaccine to protect against GBS infections.

6 Claims, 13 Drawing Sheets

Fig. 1A

```
AAGCTTATGCTTGTCAATAATCACAAATTTGTAGATCACTTCCTTTTTAGGACTGTAAAG      60
————————>
CATCCTAATTACTTTTTAAATATATTACCAGAACTAGTTGGTTTGGCCCTGGTGAGTCAT     120

GCTTATGTGACATTCATCTTTATTTTTCCTGTCTATGCGGTTATTCTTTATCAAAGAATA    180
B ————————————>
         a
GCAGAGGAAGAAAAATTATTGCAGGAAGTTATTATTCCGAATGGAAGAATGAAAGGTTAA     240

AAATAATATACCCAATTTAATATGCAGTTCATATTGGAAGGGTATACTGTAGATAAATAA     300

M  F  K  S  N  Y  E  R  K  M  R  Y  S  I          -24
AATATTGGAGGATATCGATATGTTTAAATCTAATTATGAAAGAAAAATGCGTTATTCCAT     360
                  ———>S
  R  K  F  S  V  G  V  A  S  V  A  V  A  S  L  F  M  G  S  V    -4
TCGTAAATTTAGTGTAGGAGTAGCTAGTGTAGCGGTAGCTAGTTTGTTCATGGGAAGCGT     420
  A  H  A  S  E  L  V  K  D  D  S  V  K  T  T  E  V  A  A  K    17
TGCTCATGCAAGTGAGCTTGTAAAGGACGATAGTGTGAAGACTACCGAGGTTGCAGCTAA     480
         ———>P
  P  Y  P  S  M  A  Q  T  D  Q  G  N  N  S  S  S  E  L  E       37
GCCCTATCCAAGTATGGCTCAAACAGATCAAGGAAATAATTCATCATCCTCGGAACTTGA     540
  T  T  K  M  E  I  P  T  T  D  I  K  K  A  V  E  P  V  E  K    57
GACAACAAAGATGGAAATTCCTACAACAGACATAAAAAAAGCTGTTGAACCGGTCGAGAA     600
  T  A  G  E  T  S  A  T  D  T  G  K  R  E  K  Q  L  Q  Q  W    77
AACAGCTGGGGAAACATCTGCCACTGATACTGGAAAACGAGAGAAACAATTACAACAATG     660
  K  N  N  L  K  N  D  V  D  N  T  I  L  S  H  E  Q  K  N  E    97
GAAAAATAATCTAAAAAATGATGTGGATAACACAATTCTATCTCATGAACAGAAAAATGA     720
  F  K  T  K  I  D  E  T  N  D  S  D  A  L  L  E  L  E  N  Q    117
GTTTAAAACAAAAATTGATGAAACAAATGATTCTGATGCATTATTAGAATTAGAAAATCA     780
  F  N  E  T  N  R  L  L  H  I  K  Q  H  E  E  V  E  K  D  K    137
ATTTAACGAAACTAATAGACTGTTACACATCAAACAACATGAAGAAGTTGAGAAAGATAA     840
  K  A  K  Q  Q  K  T  L  K  Q  S  D  T  K  V  D  L  S  N  I    157
GAAAGCTAAGCAACAGAAAACTCTGAAACAGTCAGATACGAAAGTAGATCTAAGCAATAT     900
  D  K  E  L  N  H  Q  K  S  Q  V  E  K  M  A  E  Q  K  G  I    177
TGACAAAGAGCTTAATCATCAAAAAAGTCAAGTTGAAAAAATGGCAGAGCAAAAGGGAAT     960
  T  N  E  D  K  D  S  M  L  K  K  I  E  D  I  R  K  Q  A  Q    197
CACAAATGAAGATAAAGATTCTATGCTGAAAAAAATCGAAGATATTCGTAAACAAGCTCA    1020
  Q  A  D  K  K  E  D  A  E  V  K  V  R  E  E  L  G  K  L  F    217
ACAAGCAGATAAAAAAGAAGATGCCGAAGTAAAGGTTCGTGAAGAACTAGGTAAACTCTT    1080
                          <——————————S
                              b
  S  S  T  K  A  G  L  D  Q  E  I  Q  E  H  V  K  K  E  T  S    237
TAGTTCAACTAAAGCTGGTCTGGATCAAGAAATTCAAGAGCATGTGAAGAAAGAAACGAG    1140
  S  E  E  N  T  Q  K  V  D  E  H  Y  A  N  S  L  Q  N  L  A    257
TAGTGAGGAAAATACTCAGAAAGTTGATGAACACTATGCTAATAGCCTTCAGAACCTTGC    1200
```

Fig. 1B

```
         Q   K   S   L   E   E   L   D   K   A   T   T   N   E   Q   A   T   Q   V   K      277
TCAAAAATCTCTTGAAGAACTAGATAAGGCAACTACCAATGAACAAGCTACACAAGTTAA                                1260

N   Q   F   L   E   N   A   Q   K   L   K   E   I   Q   P   L   I   K   E   T      297
AAATCAATTCTTAGAAAACGCTCAAAAGCTCAAAGAAATACAACCTCTTATCAAAGAAAC                                1320

N   V   K   L   Y   K   A   M   S   E   S   L   E   Q   V   E   K   E   L   K      317
GAATGTGAAATTGTATAAGGCTATGAGTGAGAGCTTGGAGCAGGTTGAGAAGGAATTAAA                                1380

H   N   S   E   A   N   L   E   D   L   V   A   K   S   K   E   I   V   R   E      337
ACATAATTCGGAAGCTAATTTAGAAGATTTGGTTGCGAAATCTAAAGAAATCGTAAGAGA                                1440

Y   E   G   K   L   N   Q   S   K   N   L   P   E   L   K   Q   L   E   E   E      357
ATACGAAGGAAAACTTAATCAATCTAAAAATCTTCCAGAATTAAAGCAACTAGAAGAGGA                                1500
                                                               S

A   H   S   K   L   K   Q   V   V   E   D   F   R   K   K   F   K   T   S   E      377
AGCTCATTCGAAGTTGAAACAAGTTGTGGAGGATTTTAGAAAAAAATTTAAAACGTCAGA                                1560
     C

Q   V   T   P   K   K   R   V   K   R   D   L   A   A   N   E   N   N   Q   Q      397
GCAAGTGACACCAAAAAAACGTGTCAAACGAGATTTAGCTGCTAATGAAAATAATCAACA                                1620

K   I   E   L   T   V   S   P   E   N   I   T   V   Y   E   G   E   D   V   K      417
AAAGATTGAGTTAACAGTTTCACCAGAGAATATCACTGTATATGAAGGTGAAGACGTGAA                                1680

F   T   V   T   A   K   S   D   S   K   T   T   L   D   F   S   D   L   L   T      437
ATTTACAGTCACAGCTAAAAGTGATTCGAAGACGACGTTGGACTTCAGTGATCTTTTAAC                                1740

K   Y   N   P   S   V   S   D   R   I   S   T   N   Y   K   T   N   T   D   N      457
AAAATATAATCCGTCTGTATCAGATAGAATTAGTACAAATTATAAGACTAACACGGATAA                                1800

H   K   I   A   E   I   T   I   K   N   L   K   L   N   E   S   Q   T   V   T      477
TCATAAGATTGCCGAAATCACTATCAAGAATTTGAAGCTAAATGAAAGTCAAACAGTGAC                                1860

L   K   A   K   D   D   S   G   N   V   V   E   K   T   F   T   I   T   V   Q      497
TCTAAAAGCTAAAGATGATTCTGGCAATGTAGTTGAAAAAACATTCACTATTACAGTGCA                                1920

→ K   K   E   E   K   Q   V   P   K   T   P   E   Q   K   D   S   K   T   E   E      517
AAAGAAAGAGGAGAAACAAGTTCCTAAAACACCAGAGCAGAAAGATTCTAAAACGGAAGA                                1980

K   V   P   Q   E   P   K   S   N   D   K   N   Q   L   E   L   I   K   S          537
AAAGGTTCCTCAAGAACCAAAATCAAATGACAAGAATCAATTACAAGAGTTGATTAAATC                                2040

A   Q   Q   E   L   E   K   L   E   K   A   I   K   E   L   M   E   Q   P   E      557
AGCTCAACAAGAACTGGAAAAGTTAGAAAAAGCAATAAAAGAATTAATGGAGCAACCAGA                                2100

I   P   S   N   P   E   Y   G   I   Q   K   S   I   W   E   S   Q   K   E   P      577
GATTCCATCCAATCCAGAGTATGGTATTCAAAAATCTATTTGGGAGTCACAAAAAGAGCC                                2160

I   Q   E   A   I   T   S   F   K   K   I   I   G   D   S   S   S   K   Y   Y      597
TATCCAGGAAGCCATAACAAGTTTTAAGAAGATTATTGGTGATTCATCTTCAAAATACTA                                2220

T   E   H   Y   F   N   K   Y   K   S   D   F   M   N   Y   Q   L   H   A   Q      617
CACAGAGCACTATTTTAACAAATATAAATCTGATTTTATGAATTATCAACTTCATGCACA                                2280

M   E   M   L   T   R   K   V   V   Q   Y   M   N   K   Y   P   D   N   A   E      637
AATGGAGATGCTGACTAGAAAAGTGGTTCAGTATATGAACAAATATCCTGATAATGCAGA                                2340
```

Fig. 1C

```
            I   K   K   I   F   E   S   D   M   K   R   T   K   E   D   N   Y   G   S   L       657
        AATTAAAAAGATATTTGAGTCAGATATGAAGAGAACGAAAGAAGATAATTACGGAAGTTT                              2400

E   N   D   A   L   K   G   Y   F   E   K   Y   F   L   T   P   F   N   K   I       677
        AGAAAATGATGCTTTGAAAGGCTATTTTGAGAAATATTTCCTTACACCATTTAATAAAAT                              2460

K   Q   I   V   D   D   L   D   K   K   V   E   Q   D   Q   P   A   P   I   P       697
        TAAGCAGATTGTAGATGATTTGGATAAAAAAGTAGAACAAGATCAGCCAGCACCAATTCC                              2520

E   N   S   E   M   D   Q   A   K   E   K   A   K   I   A   V   S   K   Y   M       717
        GGAAAATTCAGAAATGGATCAGGCTAAGGAAAAGGCTAAGATTGCTGTATCGAAGTATAT                              2580

S   K   V   L   D   G   V   H   Q   H   L   Q   K   K   N   N   S   K   I   V       737
        GAGTAAGGTTTTAGATGGAGTTCATCAACATCTGCAGAAGAAAAATAACAGTAAAATTGT                              2640

D   L   F   K   E   L   E   A   I   K   Q   Q   T   I   F   D   I   D   N   A       757
        TGATCTTTTTAAGGAACTTGAAGCGATTAAACAACAAACTATTTTTGATATTGACAATGC                              2700

K   T   E   V   E   I   D   N   L   V   H   D   A   F   S   K   M   N   A   T       777
        AAAGACTGAAGTAGAGATTGATAACTTAGTACACGATGCATTCTCAAAAATGAATGCTAC                              2760

V   A   K   F   Q   K   G   L   E   T   N   P   E   T   P   D   T   P   K           797
        TGTTGCTAAATTTCAAAAAGGTCTAGAGACAAATACGCCAGAAACTCCAGATACACCGAA                              2820

I   P   E   L   P   Q   A   P   D   T   P   Q   A   P   D   T   P   H   V   P       817
        GATTCCAGAGCTACCTCAAGCCCCAGATACACCGCAGGCTCCAGACACACCGCATGTTCC                              2880

E   S   P   K   A   P   E   A   P   R   V   P   E   S   P   K   T   P   E   A       837
        GGAATCACCAAAGGCCCCAGAAGCACCGCGTGTTCCGGAATCACCAAAGACTCCAGAAGC                              2940

P   H   V   P   E   S   P   K   A   P   E   A   P   R   V   P   E   S   P   K       857
        ACCGCATGTTCCGGAATCACCAAAGGCCCCAGAAGCACCGCGTGTTCCGGAATCACCAAA                              3000

T   P   E   A   P   H   V   P   E   S   P   K   T   P   E   A   P   K   I   P       877
        GACTCCAGAAGCACCGCATGTTCCGGAATCACCAAAGACTCCAGAAGCACCAAAGATTCC                              3060

E   P   P   K   T   P   D   V   P   K   L   P   D   V   P   K   L   P   D   V       897
        GGAACCCCCTAAGACTCCAGACGTCCCTAAGCTTCCAGACGTCCCTAAGCTTCCAGACGT                              3120

P   K   L   P   D   A   P   K   L   P   D   G   L   N   K   V   G   Q   A   V       917
        CCCTAAGCTTCCAGATGCACCGAAGTTACCAGATGGGTTAAATAAAGTTGGACAAGCAGT                              3180

F   T   S   T   D   G   N   T   K   V   T   V   V   F   D   K   P   T   D   A       937
        ATTTACATCAACTGATGGAAATACTAAGGTTACGGTTGTATTTGATAAACCTACAGATGC                              3240

D   K   L   H   L   K   E   V   T   T   K   E   L   A   D   K   I   A   H   K       957
        TGATAAGTTACATCTCAAGGAAGTAACGACGAAAGAGTTGGCTGATAAAATTGCTCATAA                              3300

T   G   G   T   V   R   V   F   D   L   S   L   S   K   G   G   K   E   T           977
        AACAGGAGGAGGAACAGTTCGTGTGTTTGACTTATCTCTTTCTAAAGGAGGCAAGGAAAC                              3360

H   V   N   G   E   R   T   V   R   L   A   L   G   Q   T   G   S   D   V   H       997
        ACATGTCAATGGAGAACGAACTGTTCGGCTCGCGCTTGGGCAGACTGGCTCAGATGTTCA                              3420

V   Y   H   V   K   E   N   G   D   L   E   R   I   P   S   K   V   E   N   G      1017
        CGTCTATCACGTAAAGGAAAATGGCGACCTTGAGCGTATTCCTTCTAAAGTTGAAAATGG                              3480
```

Fig. 1D

```
   Q   V   V   F   K   T   N   H   F   S   L   F   A   I   K   T   L   S   K   D        1037
GCAAGTTGTTTTTAAAACGAACCACTTCAGTTTGTTTGCGATTAAGACACTTTCTAAGGA                              3540
   Q   N   V   T   P   P   K   Q   T   K   P   S   T   Q   G   S   Q   V   E   I        1057
TCAAAATGTTACTCCACCGAAGCAGACTAAACCTTCTACCCAAGGCAGTCAAGTAGAGAT                              3600
   A   E   S   Q   T   G   K   F   Q   S   K   A   A   N   H   K   A   L   A   T        1077
TGCAGAGAGTCAAACTGGAAAATTCCAGAGTAAAGCAGCTAATCATAAAGCACTGGCTAC                              3660
   G   N   E   T   V   A   K   G   N   P   T   S   T   T   E   K   K   L   P   Y        1097
TGGAAATGAAACAGTGGCAAAAGGAAATCCTACATCAACAACGGAAAAGAAATTGCCATA                              3720
                                                                 → M
   T   G   V   A   S   N   L   V   L   E   I   M   G   L   L   G   L   I   G   T        1117
TACAGGAGTGGCATCTAATCTAGTTCTTGAAATTATGGGTCTCCTTGGTTTGATTGGAAC                              3780
   S   F   I   A   M   K   R   R   K   S                                                  1127
TTCATTCATCGCAATGAAAAGAAGAAAATCATGATTCAGTTTTTTAAAAATATCCACTTT                              3840

CGATATCTAGCATTTGATTGGTTATCTGTGGATGATTCTAAAGATGTTACCTATCGTTGG                              3900
     ←        d        B
TATGTAACAATTATAAGTCATTTCATATAAAAGAGGCTCTTTGTCAACTGTAGTTGGTTG                              3960

AAACAAGGCTACAAACTAGAAAGGACGCATTTTGTCCTTTCTTTTTGATGTTGAGGGCAA                              4020

TGAAAATACGCTTTTTGAAGTTTTCAAAATTCCGAAAACTAAAGATATTGTATTTGAAAA                              4080

GTTTAATGAGATGATTAGTTGCTTCCAATTTTGCGTTGGAGTAGGTTTACTGAAGGACGT                              4140

TGACGATATTCTCTTTGCTTTTGAGAATGATTTTAAAGATAGTCTGAAAAAGAGGATGAA                              4200
```

Fig. 4A

```
                    10          20          30          40          50          60
                     *           *           *           *           *           *
JB2A (806   CTTAT GTNAC ATTCA TCTTT ATTTT TCCTG TCTAT GCGGT TATTC TTTAT CAAAG AATAG 130         140         150         160         170         180
             *           *           *           *           *           *
Jerlstrom   CTTAT GTgAC ATTCA TCTTT ATTTT TCCTG TCTAT GCGGT TATTC TTTAT CAAAG AATAG>
[ 3722 ]    GAATA CANTG TAAGT AGAAA TAAAA AGGAC AGATA CGCCA ATAAG GTTTC TTATC
JB2A (806   CTTAT GTNAC ATTCA TCTTT ATTTT TCCTG TCTAT GCGGT TATTC TTTAT CAAAG AATAG 70          80          90         100         110         120
                     *           *           *           *           *           *
JB2A (806   CAGAG GAAGA AAAAT TATTG CAGGA AGTTA TTATT CCGAA TGGAA GAATG AAAGG TTAAA
            GTCTC CTTCT TTTTA ATAAC GTCCT TCAAT AATAA GGCTT ACCTT CTTAC TTTCC AATTT
            190         200         210         220         230         240
             *           *           *           *           *           *
Jerlstrom   CAGAG GAAGA AAAAT TATTG CAGGA AGTTA TTATT CCGAA TGGAA GAATG AAAGG TTAAA>
[ 3722 ]
JB2A (806   CAGAG GAAGA AAAAT TATTG CAGGA AGTTA TTATT CCGAA TGGAA GAATG AAAGG TTAAA 10          20          30          40          50
                      *           *           *           *           *
Heden            A AAAAT TATTG CAGGA AGTTA TTATT CCGAA TGGAA GAATG AAAGG TTAAA>
[ 3438 ]
JB2A (806        A AAAAT TATTG CAGGA AGTTA TTATT CCGAA TGGAA GAATG AAAGG TTAAA 130         140         150         160         170         180
             *           *           *           *           *           *
JB2A (806   AATAA TATAC CCAAT TTAAT ATGCA GTTCA TATTG GAAGG GTATA CTGTA GATAA ATAAA
            TTATT ATATG GGTTA AATTA TACGT CAAGT ATAAC CTTCC CATAT GACAT CTATT TATTT
            250         260         270         280         290         300
             *           *           *           *           *           *
Jerlstrom   AATAA TATAC CCAAT TTAAT ATGCA GTTCA TATTG GAAGG GTATA CTGTA GATAA ATAAA>
[ 3722 ]
JB2A (806   AATAA TATAC CCAAT TTAAT ATGCA GTTCA TATTG GAAGG GTATA CTGTA GATAA ATAAA 60          70          80          90         100         110
                      *           *           *           *           *           *
Heden       AATAA TATAC CCAAT TTAAT ATGCA GTTCA TATTG GAAGG GTATA CTGTA GATAA ATAAA>
[ 3438 ]
JB2A (806   AATAA TATAC CCAAT TTAAT ATGCA GTTCA TATTG GAAGG GTATA CTGTA GATAA ATAAA
```

Fig. 4B

```
                    310        320        330        340        350        360
                     *          *          *          *          *          *
JB2A (806    GCTCA TGCAA GTGAG CTTGT AAAGG ACGAT AGTGT GAAGA CTACC GAGGT TGCAG CTAAG
             CGAGT ACGTT CACTC GAACA TTTCC TGCTA TCACA CTTCT GATGG CTCCA ACGTC GATTC 430        440        450        460        470        480
Jerlstrom    GCTCA TGCAA GTGAG CTTGT AAAGG ACGAT AGTGT GAAGA CTACC GAGGT TGCAG CTAAG>
[ 3722 ]     ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806    GCTCA TGCAA GTGAG CTTGT AAAGG ACGAT AGTGT GAAGA CTACC GAGGT TGCAG CTAAG 240        250        260        270        280        290
Heden        GCTCA TGCAA GTGAG CTTGT AAAGG ACGAT AGTGT GAAGA CTACC GAGGT TGCAG CTAAG>
[ 3438 ]     ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806    GCTCA TGCAA GTGAG CTTGT AAAGG ACGAT AGTGT GAAGA CTACC GAGGT TGCAG CTAAG 190        200        210        220        230        240
                     *          *          *          *          *          *
JB2A (806    ATATT GGNGG ATATC GATAT GTTTA AATCT AATTA TGAAA ATGCG TTATT CCATT
             TATAA CCNCC TATAG CTATA CAAAT TTAGA TTAAT ACTTT CTTTT TACGC AATAA GGTAA 310        320        330        340        350        360
Jerlstrom    ATATT GGaGG ATATC GATAT GTTTA AATCT AATTA TGAAA ATGCG TTATT CCATT>
[ 3722 ]     ~~~~~ ~~-~~ ~~~~~ ~~~~~ ~~~~~ ~~~~~ ~~~~~ ~~~~~ ~~~~~ ~~~~~ ~~~~~

JB2A (806    ATATT GGNGG ATATC GATAT GTTTA AATCT AATTA TGAAA ATGCG TTATT CCATT 120        130        140        150        160        170
Heden        ATATT GGaGG ATATC GATAT GTTTA AATCT AATTA TGAAA ATGCG TTATT CCATT>
[ 3438 ]     ~~~~~ ~~-~~ ~~~~~ ~~~~~ ~~~~~ ~~~~~ ~~~~~ ~~~~~ ~~~~~ ~~~~~ ~~~~~

JB2A (806    ATATT GGNGG ATATC GATAT GTTTA AATCT AATTA TGAAA ATGCG TTATT CCATT 250        260        270        280        290        300
                     *          *          *          *          *          *
JB2A (806    CGTAA ATTTA GTGTA GGAGT AGCTA GTGTA GCGGT AGCTA GTTTA TTCAT GGGAA GCGTT
             GCATT TAAAT CACAT CCTCA TCGAT CACAT CGCCA TCGAT CAAAT AAGTA CCCTT CGCAA 370        380        390        400        410        420
Jerlstrom    CGTAA ATTTA GTGTA GGAGT AGCTA GTGTA GCGGT AGCTA GTTTg TTCAT GGGAA GCGTT>
[ 3722 ]     ~~~~~ ~~~~~ ~~~~~ ~~~~~ ~~~~~ ~~~~~ ~~~~~ ~~~~~ ~~~~v ~~~~~ ~~~~~ ~~~~~

JB2A (806    CGTAA ATTTA GTGTA GGAGT AGCTA GTGTA GCGGT AGCTA GTTTA TTCAT GGGAA GCGTT 180        190        200        210        220        230
Heden        CGTAA ATTTA GTGTA GGAGT AGCTA GTGTA GCGGT AcgTA GTTTg TTCAT GGGAA GCGTT>
[ 3438 ]     ~~~~~ ~~~~~ ~~~~~ ~~~~~ ~~~~~ ~~~~~ ~~~~~ ~~~v~ ~~~~v ~~~~~ ~~~~~ ~~~~~

JB2A (806    CGTAA ATTTA GTGTA GGAGT AGCTA GTGTA GCGGT AGCTA GTTTA TTCAT GGGAA GCGTT
```

Fig. 4C

| | | 370 | 380 | 390 | 400 | 410 | 420 |
|---|---|---|---|---|---|---|---|
| JB2A (806 | CCCTA | TCCAA | GTATG | GCTCA | AACAG | ATCAA | GGAAA | TAATT | CATCA | TCCTC | GGAAC | TTGAG |
| | GGGAT | AGGTT | CATAC | CGAGT | TTGTC | TAGTT | CCTTT | ATTAA | GTAGT | AGGAG | CCTTG | AACTC |
| | | 490 | 500 | 510 | 520 | 530 | 540 |
| Jerlstrom [3722] | CCCTA TCCAA GTATG GCTCA AACAG ATCAA GGAAA TAATT CATCA TCCTC GGAAC TTGAG> |
| JB2A (806 | CCCTA TCCAA GTATG GCTCA AACAG ATCAA GGAAA TAATT CATCA TCCTC GGAAC TTGAG |
| | | 300 | 310 | 320 | 330 | 340 | 350 |
| Heden [3438] | CCCTA TCCAA GTATG GCTCA AACAG ATCAA GGAAA TAATT CATCA TCCTC GGAAC TTGAG> |
| JB2A (806 | CCCTA TCCAA GTATG GCTCA AACAG ATCAA GGAAA TAATT CATCA TCCTC GGAAC TTGAG |
| | | 430 | 440 | 450 | 460 | 470 | 480 |
| JB2A (806 | ACAAC AAAGA TGGAA ATTCC TACAA CAGAC ATAAA AAAAG CTGTT GAACC GGTCG AGAAA |
| | TGTTG TTTCT ACCTT TAAGG ATGTT GTCTG TATTT TTTTC GACAA CTTGG CCAGC TCTTT |
| | | 550 | 560 | 570 | 580 | 590 | 600 |
| Jerlstrom [3722] | ACAAC AAAGA TGGAA ATTCC TACAA CAGAC ATAAA AAAAG CTGTT GAACC GGTCG AGAAA> |
| JB2A (806 | ACAAC AAAGA TGGAA ATTCC TACAA CAGAC ATAAA AAAAG CTGTT GAACC GGTCG AGAAA |
| | | 360 | 370 | 380 | 390 | 400 | 410 |
| Heden [3438] | ACAAC AAAGA TGGAA ATTCC TACAA CAGAC ATAAA AAAAG CTGTT GAACC GGTCG AGAAA> |
| JB2A (806 | ACAAC AAAGA TGGAA ATTCC TACAA CAGAC ATAAA AAAAG CTGTT GAACC GGTCG AGAAA |
| | | 490 | 500 | 510 | 520 | 530 | 540 |
| JB2A (806 | ACAGC TGGGG AAACA TCTGC CACTG ATACT GGAAA ACGAG AGAAA CAATT ACAAC AATGG |
| | TGTCG ACCCC TTTGT AGACG GTGAC TATGA CCTTT TGCTC TCTTT GTTAA TGTTG TTACC |
| | | 610 | 620 | 630 | 640 | 650 | 660 |
| Jerlstrom [3722] | ACAGC TGGGG AAACA TCTGC CACTG ATACT GGAAA ACGAG AGAAA CAATT ACAAC AATGG> |
| JB2A (806 | ACAGC TGGGG AAACA TCTGC CACTG ATACT GGAAA ACGAG AGAAA CAATT ACAAC AATGG |
| | | 420 | 430 | 440 | 450 | 460 | 470 |
| Heden [3438] | ACAGC TGGGG AAACA TCTGC CACTG ATACT GGAAA ACGAG AGAAA CAATT ACAAC AATGG> |
| JB2A (806 | ACAGC TGGGG AAACA TCTGC CACTG ATACT GGAAA ACGAG AGAAA CAATT ACAAC AATGG |

Fig. 4D

```
                   550        560        570        580        590        600
                    *          *          *          *          *          *
JB2A (806     AAAAA TAATC TAAAA AATGA TGTGG ATAAC ACAAT TCTAT CTCAT GAACA GAAAA ATGAG
              TTTTT ATTAG ATTTT TTACT ACACC TATTG TGTTA AGATA GAGTA CTTGT CTTTT TACTC 670        680        690        700        710        720
Jerlstrom     AAAAA TAATC TAAAA AATGA TGTGG ATAAC ACAAT TCTAT CTCAT GAACA GAAAA ATGAG>
[ 3722 ]      ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806     AAAAA TAATC TAAAA AATGA TGTGG ATAAC ACAAT TCTAT CTCAT GAACA GAAAA ATGAG 480        490        500        510        520        530
Heden         AAAAA TAATC TAAAA AATGA TGTGG ATAAC ACAAT TCTAT CTCAT GAACA GAAAA ATGAG>
[ 3438 ]      ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806     AAAAA TAATC TAAAA AATGA TGTGG ATAAC ACAAT TCTAT CTCAT GAACA GAAAA ATGAG
                   610        620        630        640        650        660
                    *          *          *          *          *          *

JB2A (806     TTTAA AACAA AAATT GATGA AACAA ATGAT TCTGA TGCAT TATTA GAATT AGAAA ATCAA
              AAATT TTGTT TTTAA CTACT TTGTT TACTA AGACT ACGTA ATAAT CTTAA TCTTT TAGTT 730        740        750        760        770        780
Jerlstrom     TTTAA AACAA AAATT GATGA AACAA ATGAT TCTGA TGCAT TATTA GAATT AGAAA ATCAA>
[ 3722 ]      ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806     TTTAA AACAA AAATT GATGA AACAA ATGAT TCTGA TGCAT TATTA GAATT AGAAA ATCAA 540        550        560        570        580        590
Heden         TTTAA AACAA AAATT GATGA AACAA ATGAT TCTGA TGCAT TATTA GAATT AGAAA ATCAA>
[ 3438 ]      ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806     TTTAA AACAA AAATT GATGA AACAA ATGAT TCTGA TGCAT TATTA GAATT AGAAA ATCAA
                   670        680        690        700        710        720
                    *          *          *          *          *          *

JB2A (806     TTTAA CGAAA CTAAT AGACT GTTAC ACATC AAACA ACATG AAGAA GTTGA GAAAG ATAAG
              AAATT GCTTT GATTA TCTGA CAATG TGTAG TTTGT TGTAC TTCTT CAACT CTTTC TATTC 790        800        810        820        830        840
Jerlstrom     TTTAA CGAAA CTAAT AGACT GTTAC ACATC AAACA ACATG AAGAA GTTGA GAAAG ATAAG>
[ 3722 ]      ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806     TTTAA CGAAA CTAAT AGACT GTTAC ACATC AAACA ACATG AAGAA GTTGA GAAAG ATAAG 600        610        620        630        640        650
Heden         TTTAA CGAAA CTAAT AGACT GTTAC ACATC AAACA ACATG AAGAA GTTGA GAAAG ATAAG>
[ 3438 ]      ~~~~~ ~~~~~ ~~~~~ ~~~~~ ~~~~~ ~~~~~ ~~~~~ ~~~~~ ~~~~~ ~~~~~ ~~~~~ ~~~~~

JB2A (806     TTTAA CGAAA CTAAT AGACT GTTAC ACATC AAACA ACATG AAGAA GTTGA GAAAG ATAAG
```

Fig. 4E

```
               730        740        750        760        770        780
                 *          *          *          *          *          *
JB2A (806   AAAGC TAAGC AACAG AAAAC TCTGA AACAG TCAGA TACGA AAGTA GATCT AAGCA ATATT
            TTTCG ATTCG TTGTC TTTTG AGACT TTGTC AGTCT ATGCT TTCAT CTAGA TTCGT TATAA 850        860        870        880        890        900
Jerlstrom   AAAGC TAAGC AACAG AAAAC TCTGA AACAG TCAGA TACGA AAGTA GATCT AAGCA ATATT>
[ 3722 ]    ^^^^^ ^^^^^ ^^^^^ ^^^^^ ^^^^^ ^^^^^ ^^^^^ ^^^^^ ^^^^^ ^^^^^ ^^^^^ ^^^^^
JB2A (806   AAAGC TAAGC AACAG AAAAC TCTGA AACAG TCAGA TACGA AAGTA GATCT AAGCA ATATT 660        670        680        690        700        710
Heden       AAAGC TAAGC AACAG AAAAC TCTGA AACAG TCAGA TACGA AAGTA GATCT AAGCA ATATT>
[ 3438 ]    ^^^^^ ^^^^^ ^^^^^ ^^^^^ ^^^^^ ^^^^^ ^^^^^ ^^^^^ ^^^^^ ^^^^^ ^^^^^ ^^^^^
JB2A (806   AAAGC TAAGC AACAG AAAAC TCTGA AACAG TCAGA TACGA AAGTA GATCT AAGCA ATATT 790        800        810        820        830        840
                 *          *          *          *          *          *
JB2A (806   GACAA AGAGC TTAAT CATCA AAAAA GTCAA GTTGA AAAAA TGGCA GAGCA AAAGG GAATC
            CTGTT TCTCG AATTA GTAGT TTTTT CAGTT CAACT TTTTT ACCGT CTCGT TTTCC CTTAG 910        920        930        940        950        960
Jerlstrom   GACAA AGAGC TTAAT CATCA AAAAA GTCAA GTTGA AAAAA TGGCA GAGCA AAAGG GAATC>
[ 3722 ]    ^^^^^ ^^^^^ ^^^^^ ^^^^^ ^^^^^ ^^^^^ ^^^^^ ^^^^^ ^^^^^ ^^^^^ ^^^^^ ^^^^^
JB2A (806   GACAA AGAGC TTAAT CATCA AAAAA GTCAA GTTGA AAAAA TGGCA GAGCA AAAGG GAATC 720        730        740        750        760        770
Heden       GACAA AGAGC TTAAT CATCA AAAAA GTCAA GTTGA AAAAA TGGCA GAGCA AAAGG GAATC>
[ 3438 ]    ^^^^^ ^^^^^ ^^^^^ ^^^^^ ^^^^^ ^^^^^ ^^^^^ ^^^^^ ^^^^^ ^^^^^ ^^^^^ ^^^^^
JB2A (806   GACAA AGAGC TTAAT CATCA AAAAA GTCAA GTTGA AAAAA TGGCA GAGCA AAAGG GAATC
```

Fig. 4F

```
                    850       860       870       880       890       900
                     *         *         *         *         *         *
JB2A  (806    ACAAA TGAAG ATAAA GATNC TATGC TGAAA AAAAT CGAAG ATATT CGTAA ACAAG CTCAA
              TGTTT ACTTC TATTT CTANG ATACG ACTTT TTTTA GCTTC TATAA GCATT TGTTC GAGTT 970       980       990      1000      1010      1020
Jerlstrom     ACAAA TGAAG ATAAA GAttC TATGC TGAAA AAAAT CGAAG ATATT CGTAA ACAAG CTCAA>
[ 3722 ]      ^^^^^ ^^^^^ ^^^^^ ^^^_^ ^^^^^ ^^^^^ ^^^^^ ^^^^^ ^^^^^ ^^^^^ ^^^^^ ^^^^^

JB2A  (806    ACAAA TGAAG ATAAA GATNC TATGC TGAAA AAAAT CGAAG ATATT CGTAA ACAAG CTCAA 780       790       800       810       820       830
Heden         ACAAA TGAAG ATAAA GAttC TATGC TGAAA AAAAT CGAAG ATATT CGTAA ACAAG CTCAA>
[ 3438 ]      ^^^^^ ^^^^^ ^^^^^ ^^^_^ ^^^^^ ^^^^^ ^^^^^ ^^^^^ ^^^^^ ^^^^^ ^^^^^ ^^^^^

JB2A  (806    ACAAA TGAAG ATAAA GATNC TATGC TGAAA AAAAT CGAAG ATATT CGTAA ACAAG CTCAA 910       920       930
                     *         *         *
JB2A  (806    CAAGC AGATA AAAAA GNAGA TGCCG AAGTA AAGGT T
              GTTCG TCTAT TTTTT CNTCT ACGGC TTCAT TTCCA A 1030      1040      1050
Jerlstrom     CAAGC AGATA AAAAA GaAGA TGCCG AAGTA AAGGT T>
[ 3722 ]      ^^^^^ ^^^^^ ^^^^^ ^_^^^ ^^^^^ ^^^^^ ^^^^^ <

JB2A  (806    CAAGC AGATA AAAAA GNAGA TGCCG AAGTA AAGGT T 840       850       860
Heden         CAAGC AGATA AAAAA GaAGA TGCCG AAGTA AAGGT T>
[ 3438 ]      ^^^^^ ^^^^^ ^^^^^ ^_^^^ ^^^^^ ^^^^^ ^^^^^ <

JB2A  (806    CAAGC AGATA AAAAA GNAGA TGCCG AAGTA AAGGT T
```

CLONING OF NON-IGA FC BINDING FORMS OF THE GROUP B STREPTOCOCCAL BETA ANTIGENS

CROSS-REFERENCE TO RELATED APPLICATION

This is a continuation of application Ser. No. 08/242,932, filed May 16, 1994, now U.S. Pat. No. 5,595,740.

BACKGROUND OF THE INVENTION

Group B streptococci (GBS) are important human pathogens. These bacteria are increasingly being recognized as disease causing agents in adults, particularly in immunocompromised individuals; however, it is as the infectious agent of over 40% of all cases of neonatal sepsis in the U.S. which caused GBS to be recognized by the National Academy of Sciences in 1985 as the fourth most important cause of preventable infectious morbidity in this country. There are over 12,000 cases of GBS sepsis in the U.S. annually, resulting in over 2,500 infant deaths and 1,350 cases of permanent neurologic damage. In addition, pregnancy-related morbidity occurs in nearly 50,000 women each year. One recent review article estimated the direct cost per year of GBS disease in this country at over $726 million. No GBS vaccine is currently available, yet it has been estimated that over 94% of the cost due to group B streptococcal disease could potentially be avoided by the development of an effective maternal vaccine.

In addition to the group B specific carbohydrate antigen which delineates GBS from other streptococcal species, these bacteria are serotyped based on the presence of one of seven known type-specific carbohydrate antigens expressed on their surfaces. These are called Ia, Ib, II, III, IV, V, and VI. In addition, a number of protein antigens known collectively as C proteins have been identified. These are designated as alpha, beta, gamma, and delta. The genes encoding the alpha and beta antigens have been cloned (Cleat and Timmis, 1987; Michel et al., 1991) and sequenced (Jerlstrom et al., 1991; Heden et al., 1991; Michel et al., 1992), and the beta antigen has been shown by a number of researchers to interact specifically, but in a non-immune manner, with the Fc region of human IgA (Russell-Jones and Gotschlich, 1984; Russell-Jones et al., 1984; Brady et al., 1989; Anthony et al., 1990; Lindahl et al., 1990; Kvam et al., 1992). The distribution of specific C protein antigens among strains of particular carbohydrate serotypes has been partially described in the literature and is complex.

A number of research groups have reported that greater than half of all cases of neonatal sepsis are caused by type III organisms, whereas type III organisms account for less than 25% of the organisms isolated from healthy colonized infants and pregnant women. There is a greater interest in protection against serotype III GBS, although none of the serotypes are considered to be benign. The only C protein antigen commonly associated with type III GBS is the delta antigen (Brady et al., 1989; Chun et al., 1991).

Low levels of maternal IgG antibodies to GBS serotype-specific carbohydrate antigens have been shown to be correlated with disease susceptibility in neonates (Baker et al., 1978; Fisher et al., 1983). Unfortunately, many carbohydrate antigens are poorly immunogenic in humans. This is known to be true of GBS type specific carbohydrates with the possible exception of the type II polysaccharide. Development of a vaccine that is effective against multiple serotypes of GBS is considered to be of paramount importance in disease prevention. The full-length GBS beta antigen is a polypeptide of approximately 130,000 daltons. It has been reported to be immunogenic and to elicit the formation of protective antibodies in animal models (Michel et al., 1991; Madoff et al., 1992). However, the potential for the use of the β antigen as a vaccine is substantially compromised because of its undesirable property of interacting with high affinity and in a non-immune manner with the Fc region of human IgA. Truncated forms of the beta antigen are secreted by certain strains of GBS in the absence of cell surface expression of the antigen, and both IgA Fc binding and non-binding forms are observed (Brady et al., 1989).

There is evidence that high levels of maternal antibodies against GBS can be passed to and protect the newborn via the placenta. Therefore, there is a great deal of interest in developing a maternal GBS vaccine. Although the beta antigen is known to be immunogenic (i.e., it induces the formation of protective antibodies) in rabbits and mice, it would be dangerous to include in a human vaccine component which can bind to a human protein.

Therefore, an object of the subject invention is to provide a non-IgA Fc binding form of the beta antigen of GBS.

BRIEF SUMMARY OF THE INVENTION

The subject invention pertains to the genetic manipulation of the gene encoding a GBS surface protein called the beta antigen so that it is no longer able to bind to human IgA. Specifically, a portion of the beta antigen gene essential for IgA binding by the encoded protein has been identified and deleted. The novel protein encoded by the altered beta antigen gene does not bind to IgA but does immunoreact with monospecific anti-beta antigen antisera raised against the natural beta antigen protein. This will allow the genetically engineered beta antigen of the subject invention to be used as a component in a human vaccine to protect against the serious health threat of GBS infections.

BRIEF DESCRIPTION OF THE DRAWINGS

FIG. 1. The DNA sequence of the beta antigen gene is shown. The positions of forward (a and c) and reverse (b and d) oligonucleotide primers used for the polymerase chain reaction are indicated. The location of restriction endonuclease sequences engineered into the oligonucleotide primers are also indicated (BamHI and SalI). The region of DNA between reverse primer b and forward primer c was deleted by the cloning strategy described in the text and in FIG. 2.

FIGS. 4A–4F. The sequence of the GBS strain HG806 derived insert DNA from plasmid pJB2a is shown aligned with the corresponding regions of the published beta antigen gene sequences (Jerlstron et al., 1991; Heden et al., 1991).

BRIEF DESCRIPTION OF THE SEQUENCES

Figure 2:
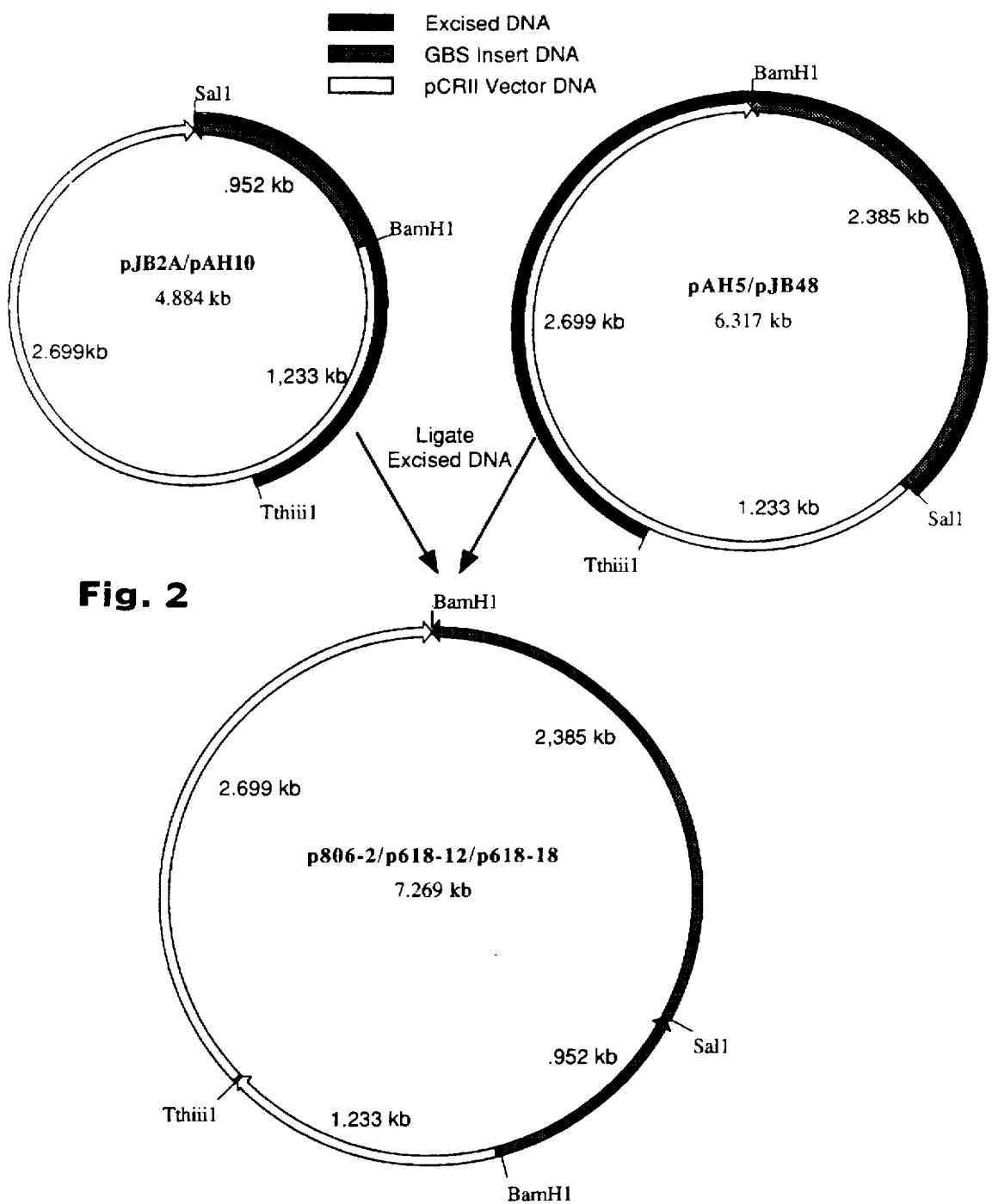
FIG. 2. The construction of the truncated beta antigen gene is shown. PCR generated DNAs (952 base pairs for pJB2a and pAH10 and 2,385 base pairs for pAH5 and pJB48) were ligated into the TA cloning site of the 3,932 base pair pCR™II vector. The positions of the BamHI (B) and SalI (S) restriction endonuclease sites engineered onto the ends of the GBS sequences and the orientation of the cloned insert DNAs are indicated. GBS-derived DNA is indicated by a bold line.

SEQ ID NO. 1 is the nucleotide sequence for the wild-type beta antigen gene published by Jerlstrom et al. (Accession Number GB2:SABAGBA) (see also FIGS. 4A–4E).

SEQ D NO. 2 is the polypeptide embodied by the subject invention (see also FIG. 1).

SEQ ID NO. 3 is the forward PCR primer a used according to the subject invention (see also FIG. 1).

SEQ ID NO. 4 is the reverse PCR primer b used according to the subject invention (see also FIG. 1).

SEQ ID NO. 5 is the forward PCR primer c used according to the subject invention (see also FIG. 1).

SEQ ID NO. 6 is the reverse PCR primer d used according to the subject invention (see also FIG. 1).

SEQ ID NO. 7 is the nucleotide sequence of the GBS strain HG806 derived insert DNA from plasmid pJB2a (see also FIGS. 4A–4E).

SEQ ID NO. 8 is the beta antigen gene sequence published by Heden et al. (Accession Number GB2:SABAC) (see also FIGS. 4A–4E).

DETAILED DISCLOSURE OF THE INVENTION

The subject invention concerns the identification and deletion of the IgA binding portion of the group B streptococcal (GBS) beta antigen. The IgA Fc binding domain of the GBS beta antigen was located by comparison of the activities of two truncated beta antigen polypeptides. The ≈55,000 dalton polypeptide secreted by GBS strain 2AR binds to the Fc region of human IgA while the ≈38,000 dalton polypeptide secreted by strain HG806 does not. Both polypeptides are reactive with rabbit anti-beta antiserum and were demonstrated to share the same amino-terminus as the mature full-length wildtype beta antigen protein. It was deduced, therefore, that either the IgA Fc binding activity of the beta antigen resides directly within the carboxy-terminal 17,000 daltons of the polypeptide expressed by strain 2AR or this region is necessary to confer IgA Fc binding activity in conjunction with the amino-terminal portion of the molecule.

A specific aspect of the subject invention concerns the construction of a novel recombinant beta antigen gene lacking that portion of DNA which encodes the IgA binding activity of the wild-type beta antigen protein. A cloning strategy was developed to construct a gene which lacked that segment of DNA believed to encode the portion of the beta antigen polypeptide necessary for non-immune binding of human IgA. Oligonucleotide primers were designed to amplify two specific segments of beta antigen DNA using the polymerase chain reaction (PCR). 0.95 kilobases (kb) of beta antigen DNA upstream as well as 2.4 kilobases of DNA downstream of the putative IgA Fc binding domain were amplified and cloned (see FIG. 1). Chromosomal DNAs from two GBS strains were used as templates for the PCR. Strain HG806 expresses the truncated ≈38,000 dalton non-IgA Fc binding molecule, while strain ss616C expresses full-length (≈130,000 dalton) IgA Fc binding beta antigen. A SalI restriction endonuclease site was engineered into the reverse and forward primers used to generate the ≈0.95 kb and ≈2.4 kb DNA segments, respectively, so that once cloned, the two segments could be ligated in frame to result in a final polypeptide product lacking approximately 150 amino acid residues in close proximity to the IgA Fc binding domain of the beta antigen. The PCR amplified gene segments for each strain were cloned into the commercially available vector pCR™II. This vector is specifically designed to accept PCR-generated DNA. Lastly, pCR™II plasmids harboring the 0.95 kb and 2.4 kb gene segments for each strain were double digested with SalI and TthIIIi restriction endonucleases. The appropriate size fragments were recovered and ligated to fuse the beta antigen gene segments in frame, as well as to reconstitute a single copy of the pCR™II vector (see FIG. 2). BamHI restriction endonuclease sequences were engineered into the forward and reverse primers used to generate the ≈0.95 and ≈2.4 kb gene segments, respectively. Therefore, the beta antigen gene constructs lacking DNA necessary to encode a functional IgA Fc binding domain can be excised from the vector by digestion with BamHI. This enables transfer of these gene constructs to any vector of choice with a BamHI sequence in its multiple cloning site. The ≈0.95 and ≈2.4 kb gene segments can be excised from their respective plasmids either by double digestion with SalI or BamII or by digestion with BstXI, which cleaves on either side of the insert in the vector DNA.

The subject invention further concerns the expression of a novel non-IgA binding polypeptide using the recombinant beta antigen gene constructs containing the region deleted by the cloning strategy. Successful PCR amplification of both the 0.95 kb and 2.4 kb beta antigen gene fragments from strain HG806 indicates that despite the expression of a markedly truncated polypeptide by this strain, no major deletions exist in the gene to account for the observed phenotype. A likely explanation for the expression of a truncated product is the existence of a nonsense mutation in this particular strain's beta antigen gene resulting in a premature stop codon. As expected, there were no premature stop codons found during sequencing of HG806-derived DNA located upstream of the putative IgA binding domain. The genetic lesion present in HG806 is most likely present in that portion of its beta antigen gene eliminated by the cloning strategy described above. Such a deletion in HG806 would therefore allow for reexpression of carboxy-terminal beta antigen. This indeed seems to be the case as the polypeptide product of the ≈3.3 kb fused gene construct is reactive with anti-beta antibodies and is substantially larger than the product of the ≈0.95 kb gene segment.

Elimination of the DNA encoding the IgA Fc binding domain results in an obliteration of IgA Fc binding activity by the gene construct derived from strain ss618C. Appropriate size gene constructs (3.3 kb) have been derived from both strains HG806 and ss618C. The polypeptides expressed by the ≈3.3 kb fused gene constructs derived from both strains HG806 and ss618C can be detected by Western immunoblotting using polyclonal rabbit antiserum recognizing the GBS beta antigen, yet no interaction of these polypeptides with biotin-labelled human myeloma IgA kappa protein has been demonstrated. These results indicate that the segment of DNA necessary for IgA Fc binding has been sufficiently disrupted to eliminate this property of the beta antigen, while the antigenic nature of the polypeptide has not been sufficiently disturbed to preclude its interaction with specific anti-beta antibodies. Since it is unacceptable to use, as a component of a vaccine, any molecule which can specifically bind with high affinity to a host protein, e.g., an immunoglobulin molecule, the construction of specifically engineered GBS beta antigen genes which eliminate this undesirable property will allow its use as both a carrier and immunogen in a GBS vaccine preparation. Therefore, the subject invention further relates to the use of the non-IgA binding beta antigen disclosed herein as an immunogenic composition to raise an immune response.

Because of the redundancy of the genetic code, a variety of different polynucleotide sequences can encode the polypeptides disclosed herein. It is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the immunological reactivity of the encoded polypeptide with anti-beta antigen antisera. In addition, the scope of the subject invention encompasses all or part of the nucleotide sequences disclosed herein, provided that the polypeptide encoded by the polynucleotide sequence does not bind to IgA but does immunoreact with the anti-beta antigen antisera.

Fragments and variants of the claimed polypeptides which do not bind to IgA but retain immunological reactivity with anti-beta antigen antisera are within the scope of the subject invention. As a person skilled in the art would appreciate, certain amino acid substitutions within the amino acid sequence of the polypeptide can be made without altering the immunological reactivity of the polypeptide. For example, amino acids may be placed in the following classes: non-polar, uncharged polar, basic, and acidic. Conservative substitutions, whereby an amino acid of one class is replaced with another amino acid of the same class, fall within the scope of the subject invention so long as the substitution does not materially alter the immunological reactivity of the polypeptide. Non-conservative substitutions are also contemplated as long as the substitution does not significantly alter the immunological reactivity of the non-IgA binding polypeptide.

The polypeptide specifically exemplified herein encompasses amino acids 1–209 and 353–1127 of the full-length wild-type GBS beta antigen as a single fusion product. As the skilled artisan will readily appreciate, the deleted region of the beta antigen could be somewhat smaller or larger than that which is exemplified herein. Variant polypeptides would be within the scope of the subject invention as long as the polypeptide did not bind to IgA but did immunoreact with anti-beta antigen antisera. For example, using the teachings provided herein, a person skilled in the art could readily prepare a polypeptide that varied from 1 to about 60 amino acids, added to or removed from, either end of the deleted region exemplified herein. For example, in a preferred embodiment, amino acids starting at about 250 can be deleted up to about amino acid 350. Preferably, any added amino acids would be the same as the corresponding amino acids of the wild-type beta antigen polypeptide. Also within the scope of the subject invention are polypeptides having amino acids added to or deleted from either the amino-terminus or carboxy-terminus of the polypeptide specifically exemplified herein. Such additions or deletions would be readily apparent to a person of ordinary skill in the art.

The polynucleotides of the subject invention can be used to express the recombinant beta antigen. They can also be used as a probe to assay for GBS infection. The polynucleotides can also be used as DNA sizing standards.

The polypeptides of the subject invention can be used to raise an immunogenic response to GBS. They can also be used as a molecular weight standards, or as an inert protein in an assay. The polypeptides can also be used to detect the presence of antibodies immunoreactive with GBS.

The polynucleotide sequences of the subject invention may be composed of either RNA or DNA. More preferably, the polynucleotide sequences are composed of DNA.

Materials and Methods

Bacterial strains and plasmids

Isolates of group B streptococci (GBS) from the clinical laboratories of Shands Hospital, J. Hillis Miller Health Science Center, University of Florida, Gainesville, Fla. were used in this study. Strain ss618 was obtained from the Centers for Disease Control (Atlanta, Ga.). Strain ss618C was selected for high levels of expression of the GBS beta antigen and IgA Fc binding activity as previously described (Brady et al., 1989). For use in serological tests, GBS were grown to a stationary phase in Todd-Hewitt broth (BBL Microbiology Systems, Cockeysville, Md.) for 18–24 hours at 37° C. Stock cultures were stored in glycerol at −70° C. The plasmid vector pCR™II (InVitrogen Corp., San Diego, Calif.) was used for cloning fragments of the GBS beta antigen gene generated using the polymerase chain reaction. Ligated pCR™II and PCR-generated beta antigen DNAs were used to transform *E. coli* INVaF' ("ONESHOT", InVitrogen Corp.) in accordance with the manufacturer's instructions. *E. coli* were grown in Luria-Bertani (LB) broth supplemented with 50 μg/ml ampicillin or kanamycin at 37° C. with aeration.

Antibodies

Rabbit antibody to type Ia, Ib, II, and III carbohydrate antigens, as well as rabbit antibody to the c-protein marker, were provided by Dr. R. Facklam (Centers for Disease Control, Atlanta, Ga.). Monospecific antiserum recognizing the GBS beta antigen was prepared by selective adsorption of the anti-c protein serum with appropriate strains expressing the alpha, gamma, and delta antigens as previously described (Brady et al., 1989). Peroxidase conjugated goat anti-rabbit IgG (whole molecule) was purchased from Cappel (Organon Teknika Corp., Westchester, Pa.)

Restriction endonucleases

Restriction endonucleases AlwNI, BspHII, BstXI DraII, HindIII, KpnI, SalI (New England BioLabs, Beverly, Mass.), BamHI, BglI, BglII, EcoRV (Promega, Madison, Wis.), Cla1 (Bethesda Research Laboratories, Gaithersburg, Md.), TthIIIi (International Biotechnologies, Inc., New Haven, Conn.), and XmnI (Stratagene, La Jolla, Callif.) were used according to the manufacturer's instructions.

Biotinylation of human IgA

Chromatographically purified human myeloma IgA kappa was purchased from Cappel (Westchester, Pa.). Protein was resuspended to a concentration of 5 mg/ml in 0.01M sodium phosphate buffer, pH 7.3. One milligram of IgA was reacted with 250 μg (10 mg/ml in dimethyl sulfoxide, Fisher Scientific, Fair Lawn, N.J.) of biotin-N-hydroxysuccinimide ester (Sigma Chemical Co., St. Louis Mo.). The reaction was performed in 0.1M sodium borate buffer, pH 8.8, in a 1.0 ml reaction volume. The mixture was rotated end over end for four hours at 4° C. The reaction was stopped by the addition of 20 μl of 1.0M $NH_4Cl$ and incubation at ambient temperature for 10 minutes. The uncoupled NHS-biotin was separated from the conjugated protein by passage over a column of "SEPHADEX" G–25M (PD≈10, Pharmacia, Piscataway, N.J.). The IgA-biotin conjugate was buffer exchanged into PBS and stored in aliquots at −20° C. Peroxidase-avidin was purchased from Sigma Chemical Co.

Dot blot assay for detection of group B streptococcal surface and secreted antigens All isolates used for this study were confirmed as GBS by screening with the "PHADEBACT" streptococcus test (Pharmacia Diagnostics, Piscataway, N.J.). Bacteria were typed using a modification of a previously described method (Brady et al., 1988. Briefly, the bacteria were grown to stationary phase at 37° C. (≈18 hours) in 10 ml Todd-Hewitt broth, harvested by centrifugation (8 minutes at 100×g), washed once with 5 ml of 0.15M phosphate buffered saline (PBS), pH 7.4, and resuspended in 2 ml of PBS. This bacteria suspension was subjected to an additional 1:40 dilution in PBS. Culture supernatants were filtered using 0.2 micron disposable filters ("ACRODISC," Gelman Sciences, Ann Arbor, Mich.) and concentrated approximately 20-fold using "MINICON" Macrosolute Concentrators (Amicon, Beverly, Mass.). Fifty microliter samples of each GBS cell suspension and 100 µl of each corresponding culture supernatant were dotted in duplicate onto a nitrocellulose membrane ("TRANSBLOT" transfer medium Bio-Rad Laboratories, Hercules, Calif.) using a "MINIFOLD I" microsample filtration manifold (Schleicher & Schuell Keene, N.H.). Wells were washed twice with 200 µl of PBS and the filter removed from the apparatus. Nitrocellulose filters were blocked by washing four times (15 minutes per wash, approximately 2 ml per cm² filter area) with PBS containing 0.25% gelatin and 0.25% "TWEEN-20" (PBS-Gel-Tw) at room temperature. Filters were then reacted for 1–3 hours with type-specific antibody (0.1 ml per cm²) diluted 1:500 in PBS-Gel-Tw and washed another four times with PBS-Gel-Tw as described above. Filters were probed overnight with peroxidase conjugated goat anti-rabbit IgG (0.1 ml per cm²) diluted 1:1000 in PBS-Gel-Tw. Filters were washed twice (15 minutes each) with PBS-Gel-Tw and twice with PBS prior to development. Reactivity was visualized by development at ambient temperature for 30 minutes in 0.1 ml per cm² of 4-chloro-1-naphthol solution (7 ml of PBS, 1 ml of 4-chloro-1-naphthol [Sigma Chemical Co.; 3 mg/ml in ice cold methanol], and 8 microliters of 30% hydrogen peroxide [Fisher Scientific]). Bacterial suspensions and culture supernatants were tested for reactivity with each GBS type-specific antiserum and monospecific anti-beta antiserum. All strains which demonstrated reactivity with anti-Ib carbohydrate typing antiserum and/or with anti-beta antiserum were subsequently tested for IgA Fc binding activity.

Dot blot assay for detection of human IgA Fc binding activity

GBS were screened for IgA Fc binding activity using the same dot blot procedure described above except that biotin-labelled human myeloma IgA kappa (1:500 dilution) was substituted for the primary antibody in the first stage of the assay and peroxidase-avidin (1:1000) was substituted for the peroxidase-conjugated secondary antibody prior to development.

Amino-terminal sequencing of truncated beta antigen polypeptides

Concentrated Todd-Hewitt broth culture supernatants containing truncated beta antigen polypeptides from GBS strains 2AR and HG806 were subjected to 10% sodium dodecyl sulfate-polyacrylamide gel electrophoresis (SDS-PAGE) as described below using 0.2M Tris, pH 8.9 as the anode buffer and 0.1M Tris, 0.1M Tricine, 0.1% SDS as the cathode buffer. Proteins were transferred to a PVDF membrane ("IMMOBILON-P," Millipore Corp., Bedford, Mass.) by electroblotting using 20% methanol, 10 mM MES buffer, pH 6.0 (2-[N-morpholino]ethanesulfonic acid, Sigma Chemical Co.). The membrane was stained with Coomassie Brilliant Blue and the blotted beta antigen band was excised and sequenced using an Applied Biosystems 470A Protein Sequencer (Foster City, Calif.).

Preparation of chromosomal DNA

GBS were grown overnight at 37° C. in 5 ml of Todd-Hewitt broth containing 20 mM DL-threonine. The next morning, 10 ml of fresh broth was added and the culture was grown for an additional 45 minutes. Then, 0.75 g of glycine was added and the culture grown for another 60 minutes. Cells were harvested by centrifugation at 7,500×g for 10 minutes and resuspended in 1 ml of sterile distilled water. The cell suspension was transferred to an Eppendorf tube and the cells pelleted by centrifugation in an Eppendorf centrifuge on high speed for 3 minutes. The cells were resuspended in 0.5 ml 5 mM EDTA, 10 mM Tris, pH 8.5, containing 25% sucrose. Six microliters of RNAse (10 mg/ml) and 70 µl of lysozyme (15 mg/ml) were added and the cells were incubated at 37° C. for 1 hour. Cells were lysed by the addition of 40 yl of 10% SDS and incubation for 20 minutes at room temperature. The mixture was vortexed briefly, followed by three extractions with 0.6 ml phenol/chloroform/isoamyl alcohol (25:24:1). The phases were separated by 5 minutes of low speed spinning in an Eppendorf centrifuge. Three addition extractions were performed with 0.5 ml chloroform/isoamyl alcohol (24:1) to remove residual phenol. The DNA containing aqueous phase was dialyzed overnight against 10 mM Tris, 2 mM EDTA, pH 8.0 at 4° C. DNA was precipitated by the addition of ⅒ volume 3M sodium acetate and 2 volumes of 95% ethanol. The pellet was washed with 70% ethanol and the DNA was resuspended in sterile distilled water to a concentration of 1 mg/ml.

Polymerase chain reaction

Oligonucleotide primers employed for the PCR corresponded to base positions 121–139 (forward primer a; SEQ ID NO. 3) and 1491–1509 (forward primer c; SEQ ID NO. 5) and complementary nucleotides corresponding to base positions 1039–1057 (reverse primer b; SEQ ID NO. 4) and 3841–3859 (reverse primer d; SEQ ID NO. 6) of the previously published sequence of the gene encoding the GBS beta antigen (Jerlstrom et al., 1991) (SEQ ID NO 1). Added to the 5' ends of forward primer a (SEQ ID NO. 3) and reverse primer d (SEQ ID NO. 6) were restriction sequences for BamHI, while SalI restriction sequences were added to the 5' ends of reverse primer b (SEQ ID NO. 11) and forward primer c (SEQ ID NO. 5). The positions of these oligonucleotide primers are shown schematically in FIG. 1. The PCR primer sequences with restriction 5 sequences underlined and the beta antigen DNA shown in boldface are as follows:

Forward primer a (SEQ ID NO. 3): 5'-GC GGATCCGCTTATGTGACATTCATC-3'

Reverse primer b (SEQ ID NO. 4): 5'-GC GTCGACAACCTTTACTTCGGCATC-3'

Forward primer c (SEQ ID NO. 5): 5'-GC GTCGACCTAGAAGAGGAAGCTCAT-3'

Reverse primer d (SEQ ID NO. 6): 5'-GC GGATCCATCAAATGCTAGATATCG-3'

PCR was carried out using approximately 50 to 100 ng of template DNA, 1 µm of each primer, and reagents included in the "TA CLONING KIT" (InVitrogen Corp.) according to the manufacturer's instructions. The reaction was carried out for 33 cycles using a Coy "TEMPCYCLER" (Coy, Ann Arbor, Mich.) with GBS strains HG806 and ss618C chromosomal DNA as templates and with the following parameters: (i) denaturation, 96° C., 30 seconds; (ii) primer annealing, 56° C., 1 minute; (iii) primer extension, 72° C., 2 minutes. An additional 5 minute primer extension step was performed after the final cycle. DNA fragments of 952 base pairs and 2,385 base pairs including the new BamHI and SalI restriction sites were predicted to be produced from this process. Products of the PCR were analyzed by electrophoresis through 0.7% agarose to confirm their size prior to cloning directly into the pCR™II vector as described below.

Cloning of PCR-generated DNA fragments

The 952 and 2,385 base pair beta antigen gene fragments produced by PCR using HG806 and ss618C chromosomal DNA as templates were ligated into the pCR™II vector. This vector is supplied in linear form with overlapping thymidine residues that are ligated to the overhanging adenosine residues on the DNA fragments that result from the PCR process. The ligated DNAs were used to transform *E. coli* INVaF ("ONESHOT," InVitrogen Corp.) according to the manufacturer's instructions. Clones were screened by blue-white selection on LB agar supplemented with 50 μg ampicillin or kanamycin and 0.75 μg of 5-bromo-4-chloro-3-indolyl-β-D-galactopyranoside (X-GAL) per ml. White colonies were picked, and plasmid DNA was prepared by the Mini-Prep procedure described below. Clones were screened for incorporation of appropriate sized inserts by digesting Mini-Prep DNA with BstXI. There are two BstXI restriction endonuclease sites approximately 20 bases upstream and downstream of the TA cloning site in the pCR™II vector. There were no BstXI sites found within either of the sequenced beta antigen genes (Jerlstrom et al, 1991; Heden et al., 1991) (SEQ ID NOS. 1 and 8, respectively). The orientation of insert DNA with respect to the vector DNA was determined by restriction endonuclease analysis. BglII and EcoRV were used for those clones having 952 bp inserts, while DraII, BspHI, and HindIII were used for those clones with 2,385 bp inserts. The following clones were chosen for use in construction of a gene encoding a non-IgA Fc binding form of the beta antigen, JB2a, AH5, AH10, and JB48. pJB2a and pAH5 represent plasmids containing 952 bp and 2,385 bp inserts derived from strain HG806, respectively; while pAH10 and pJB48 represent plasmids containing 952 bp and 2,385 bp inserts derived from ss618C, respectively. The 952 bp inserts derived from each streptococcal strain would be predicted to contain the putative promoter DNA for the beta antigen gene. The insert DNA for each of the four plasmids chosen for further work was in the opposite orientation (3' to 5') with respect to the pCR™II vector DNA (5' to 3') (see FIG. 2).

Large scale preparations of each of the four plasmids were made as described below, and each plasmid was digested with SalI and TthIIIi restriction endonucleases. SalI sites were engineered into one end each of the 952 and 2,385 bp inserts, while there is a single TthIIIi site within the pCR™II vector at nucleotide position 1567. This is illustrated schematically in FIG. 2. Digestion of pJB2a and pAH10 would be predicted to result in fragment sizes of approximately 2.2 and 2.7 kb and digestion of pAH5, and pJB48 would be predicted to result in fragment sizes of 1.2 and 5.1 kb. Ligation of the 2.2 and 5.1 kb fragments results in an in-frame fusion of the beta antigen gene segments, as well as the reconstitution of a single copy of the pCR™II vector. Approximately 20 μg of each plasmid DNA was first digested with SalI, followed by digestion with TthIIIi according to the manufacturer's instructions. The double digestions were run out on 0.7% agarose prep gels, the appropriate sized bands were excised, and the DNA was recovered by placing each gel slice in a "MICROFILTERFUGE" tube (Rainin, Woburn, Mass.), freezing at −70° C. for 30 minutes, spinning on high speed in an Eppendorf centrifuge at 4° C. for 30 minutes, and precipitating the DNA at −70° C. with 1/10 volume 3M sodium acetate and 2 volumes of 95% ethanol. The 2.2 kb fragment from pJB2a was ligated with the 5.1 kb fragment from pJB48. The ligated DNAs were used to transform *E. coli* INVaF' according to the manufacturer's instructions. Clones were screened as described above. Mini-Prep DNAs were digested with BstXI to check for the presence of a 3,337 bp insert. This represents the fusion of the 952 bp and 2,385 bp fragments by means of the SalI site engineered into each. The following clones contained appropriate-sized DNA inserts and were selected for further analysis. p816-2 represents the fusion product of pJB2a and pAH5 plasmid DNAs, while p618-12 and p618-18 represent the fusion product of pAH10 and pJB48 plasmid DNAs. Large scale plasmid preparations of p806-2, p618-12, and p618-18 were prepared as described below and each plasmid was checked against the predicted beta antigen gene sequence by restriction enzyme analysis as described below. In addition, the insert DNA from pJB2a was subjected to DNA sequence analysis at the University of Florida ICBR DNA Sequencing Core Facility using M13 forward and reverse sequencing primers.

Preparation of plasmid DNA

Large quantities of plasmid DNA were prepared using an alkaline lysis, PEG precipitation procedure. Briefly, *E. coli* harboring recombinant plasmids were grown overnight at 37° C. with aeration in 30 ml of Terrific Broth (12 g/l bacto-tryptone, 24 g/l bacto-yeast extract, 4 ml/l glycerol, 17 mM $KH_2PO_4$, 72 mM $K_2HPO_4$) containing 50 μg/ml ampicillin or kanamycin. Bacterial cells were harvested by centrifugation and resuspended in 4 ml of GTE buffer (50 mM glucose, 25 mM Tris, pH 8.0, 10 mM EDTA, pH 8.0). Cells were lysed by addition of 6 ml of freshly prepared 0.2 N NaOH containing 1% SDS and incubation on ice for 5 minutes. The solution was neutralized by the addition of 6 ml of 3.0M potassium acetate, pH 4.8, and incubation on ice for 5 minutes. Cellular debris was removed by centrifugation at 12,000×g for 10 minutes at room temperature, and the supernatant was transferred to a clean tube. RNAse was added to a final concentration of 20 μg/ml and incubated at 37° C. for 20 minutes. The supernatant was then extracted twice with ½ volume chloroform/isoamyl alcohol (24:1) and the aqueous phase transferred to a clean tube. Total DNA was precipitated by adding an equal volume of 100% isopropanol and centrifugation at 12,000×g for 10 minutes at room temperature. The DNA pellet was washed with 70% ethanol, dried under vacuum, and resuspended in 600 μl of sterile distilled water. Plasmid DNA was precipitated by first adding 160 μl of 4M NaCl and then adding 800 μl of 13% $PEG_{8000}$. After thorough mixing, the sample was incubated on ice for 20 minutes and the plasmid DNA was pelleted by centrifugation at 12,000×g for 15 minutes at 4° C. The pellet was washed with 70% ethanol, dried under vacuum, and resuspended to a concentration of 1 mg/ml in sterile distilled water.

Mini-Prep DNA was prepared to screen plasmid DNA isolated from white colonies by inoculating each colony into 2 ml of Terrific Broth containing 25 μg/ml of kanamycin and incubating overnight at 37° C. with aeration. One and a half milliliters of each overnight culture were transferred to an Eppendorf tube and the bacteria harvested by centrifugation in an Eppendorf centrifuge for 1 minute on high speed at room temperature. The supernatant was discarded and the bacteria resuspended in 100 µl lysis buffer (8% sucrose, 10 mM Tris, pH 8.0, 50 mM EDTA, pH 8.0, and 0.5% Triton X-100). Ten microliters of fresh lysozyme (10 mg/ml) and 2 µl of RNAse (10 mg/ml) were added to the cell suspension and mixed. The cells were boiled for 30 seconds and the bacterial debris pelleted by centrifugation for 5 minutes on high speed at room temperature. The pellet was removed with a sterile toothpick and the DNA precipitated by the addition of 100 µl of isopropanol at room temperature. DNA was pelleted by centrifugation for 15 minutes on high speed at room temperature. The supernatant was decanted and the pellet dried under vacuum. The DNA pellet was resuspended in 10 µl TE (10 mM Tris, 2 mM EDTA, pH 8.0).

Restriction endonuclease digestion of clones

Plasmids were purified from seven clones of interest: JB2a, AH5, AH10, JB48, 806-2, 618-12, and 618-18. Each plasmid was subjected to restriction endonuclease analysis with the enzymes listed below to confirm the digestion pattern predicted based on the published sequences of the beta antigen gene (Jerlstrom et al., 1991; Heden et al., 1991) (SEQ ID NOS. 1 and 8 respectively) and the pCR™II vector. pJB2a and pAH10 were digested with KpnI, BglI, AlwNI, XmnI, and ClaI/BssH2; pAH5 and pJB48 were digested with KpnI, DraII, AlwNI, and HindIII; and p806-2, p618-12, and p618-18 were digested with KnI, BglI, BglII, AlwNI, and ClaI/BssH2.

Sodium dodecyl sulfate-polyacrylamide gel electrophoresis and Western immunoblotting Protein samples were denatured by boiling for 5 minutes in 2% (wt/vol) sodium dodecyl sulfate, 10% glycerol (wt/vol), 0.5M Tris-HCl, pH 6.8, 0.01% bromphenol blue. Denatured proteins were electrophoresed on 7.5% or 10% polyacrylamide gel slabs at 25 mA per slab for 1 hour by the method of Laemmli (1970). Prestained molecular weight markers (Sigma Chemical Co.) were run in one lane of each gel for determination of estimated molecular weights. The proteins on the gels were transferred electrophoretically to nitrocellulose ("TRANSBLOT" transfer medium, Bio-Rad) by the method of Towbin et al. (1979). The gels and nitrocellulose filters were presoaked in 25 mM Tris, 192 mM glycine, 20% methanol (pH 8.3), assembled into a "TRANS-BLOT SD" Semi-Dry Transfer Cell (Bio-Rad) and electrophoresed for 30 minutes at 15 V. Blots were blocked and probed with rabbit anti-beta antiserum and peroxidase goat anti-rabbit IgG or biotin-labelled human myeloma IgA kappa and peroxidase-avidin as described above for the dot blot assays.

Protein samples were prepared as follows: Supernatants from GBS strains were prepared as described above for the dot blot assay. Fifteen microliters of each concentrated GBS culture supernatant was loaded per lane. Cell extracts of *E. coli* were prepared by growing 10 ml of bacteria overnight at 37° C. with aeration in LB broth containing 50 µg/ml ampicillin or kanamycin. The bacteria were harvested by centrifugation at 2,000×g for 10 minutes at room temperature. The cells were washed once with 5 ml of PBS and once with 1 ml of PBS. The cells were resuspended in 200 µl of SDS-sample buffer and boiled for 5 minutes. Cellular debris was removed by centrifugation at high speed in an Eppendorf centrifuge for 10 minutes. Fifty microliters of each cell extract were loaded per lane. The residual LB broth culture supernatant was concentrated approximately 40-fold as described above for GBS Todd-Hewitt broth culture supernatant and 50 µl of each concentrated *E. coli* culture supernatant were loaded per lane.

Following are examples which illustrate procedures, including the best mode, for practicing the invention. These examples should not be construed as limiting. All percentages are by weight and all solvent mixture proportions are by volume unless otherwise noted.

EXAMPLE 1

Identification of Beta Antigen Expression/IgA Fc Binding Activity by GBS

Fifty-three strains of group B streptococci were identified which either expressed the beta antigen or the type Ib carbohydrate on their surfaces when tested by dot blot assay. All of these strains were tested for secretion of the beta antigen into culture supernatants and were screened for surface and/or secreted IgA Fc binding activity. None of these strains were shown to express the beta antigen in the absence of IgA Fc binding activity. Therefore, the previously identified GBS strains 2AR and HG806, which secrete truncated $M_r \approx 55,000$ IgA Fc binding and $M_r \approx 38,000$ non-IgA Fc binding forms of the beta antigen, respectively, in the absence of surface expression, were chosen for further characterization. The GBS strain ss618C, which expresses high levels of full-length IgA Fc binding beta antigen $M_r \approx 130,000$, was also chosen as a candidate strain for cloning experiments.

EXAMPLE 2

Amino-Terminal Sequencing of Truncated Forms of the Beta Antigen

In order to determine the approximate location of IgA Fc binding activity within the GBS beta antigen protein, amino-terminal sequencing was performed on the two truncated beta antigen polypeptides secreted by GBS strains 2AR and HG806. The ten amino-terminal residues of the $M_r \approx 55,000$ IgA Fc binding polypeptide expressed by strain 2AR corresponds to the amino-terminal sequence predicted for the mature full-length beta antigen protein following cleavage of a thirty-seven amino acid residue signal sequence (Jerlstrom et al., 1991; Heden et al., 1991). The amino-terminal residues of the $M_r \approx 38,000$ non-IgA Fc binding polypeptide expressed by strain HG806 were also the same. It is therefore reasonable to conclude that the IgA Fc binding domain of the GBS beta antigen lies within the carboxy-terminal 17,000 daltons of the polypeptide expressed by strain 2AR. Alternatively, the IgA Fc binding domain may lie at least in part within the 38,000 dalton polypeptide expressed by HG806, but the additional 17,000 daltons expressed by 2AR may be necessary to achieve the proper conformation to confer IgA Fc binding activity.

EXAMPLE 3

Construction of a Gene Encoding a Non-IgA Fc Binding Form of the GBS Beta Antigen Oligonucleotide primers were designed so that DNA upstream and downstream of the putative IgA Fc binding domain would be amplified by the polymerase chain reaction (PCR). The location of these primers is shown in FIG. 1. Also illustrated is the DNA segment which was eliminated from the beta antigen gene by this cloning strategy. Added to the 5' ends of forward primer a and reverse primer d were restriction sequences for BamHI, while SalI restriction sequences were added to the 5' ends of reverse primer b (SEQ ID NO. 4) and forward primer c (SEQ ID NO. 5). The positions of these engineered restriction sites are also indicated in FIG. 1.

Chromosomal DNA from GBS strains HG806 and ss618C were used as templates for the PCR reactions. A DNA fragment of 952 base pairs including the BamHI and SalI restriction sites was predicted to result from the use of forward primer a (SEQ ID NO. 3) and reverse primer b (SEQ ID NO. 4), while a fragment containing 2,385 base pairs was predicted to result from the use of forward primer c (SEQ ID NO. 5) and reverse primer d (SEQ ID NO. 6). These two fragments were successfully generated by PCR using chromosomal DNA from both GBS strains as templates. The products of the PCR were analyzed by electrophoresis through 0.7% agarose gel to confirm their sizes prior to cloning directly into the pCR™II vector.

The 952 bp and 2,385 bp PCR-generated DNAs were ligated to the linear pCR™II vector and used to transform *E. coli* INVaF'. Clones were screened by blue-white selection. White colonies were picked and screened by Mini-Prep for the presence of insert DNA. Those clones containing inserts were subjected to restriction analysis with BstXI, which cuts on either side of insert DNA in the pCR™II vector. Those clones with appropriate-sized inserts, approximately 0.95 kb or 2.4 kb, were subjected to further restriction endonuclease analysis. Clones with ≈0.95 kb inserts were mapped with BglI and EcoRV restriction endonucleases, while clones with ≈2.4 kb inserts were mapped with HindIII, DraIII, and BspHI restriction endonucleases. This enabled the determination of the orientation of the insert DNA with respect to the vector DNA in each clone. Four clones were selected for further genetic manipulation. JB2 and AH10 represented the ≈0.95 kb clones derived from GBS strains HG806 and ss618C, respectively. AH5 and JB48 represented the ≈2.4 kb clones derived from GBS strains HG806 and ss618C, respectively. The insert DNA in all four of these clones was found to be in the opposite orientation (3' to 5') as the vector DNA (5' to 3').

The strategy for ligation of the ≈0.95 kb and ≈2.4 kb DNA fragments and reconstruction of a single copy of the pCR™II vector is shown in FIG. 2. Plasmid DNAs from each of the four clones were digested with both SalI and TthIIIi restriction endonucleases. Appropriate digestion fragments from plasmids derived from GBS strains HG806 and ss618C were purified and the ≈0.95 kb and ≈2.4 kb gene segments were ligated in frame via the SalI site engineered into one end of each. Ligation via the TthIIIi site at the other end of the restriction fragment resulted in reconstitution of an intact pCR™II vector. Restriction fragments from pJB2a (≈0.95 kb, HG806) and pAH10 (≈0.95 kb, ss618C) were ligated to pAH5 (≈2.4 kb, HG806) and pJB48 (≈2.4 kb, ss618C), respectively. The ligated DNAs were again used to transform *E. coli* INVaF', and white colonies were screened by Mini-Prep and BstXI digestion for the presence of appropriate-sized inserts (3,337 base pairs). Three clones which contained ≈3.3 kb inserts were chosen for further study. These included 806-2, constructed by the fusion of pJB2a and pAH5, and 618-12 and 618-18, constructed by the fusion of pAH10 and pJB48.

EXAMPLE 4

Restriction Endonuclease Analysis of Plasmid DNA

Figure 3:
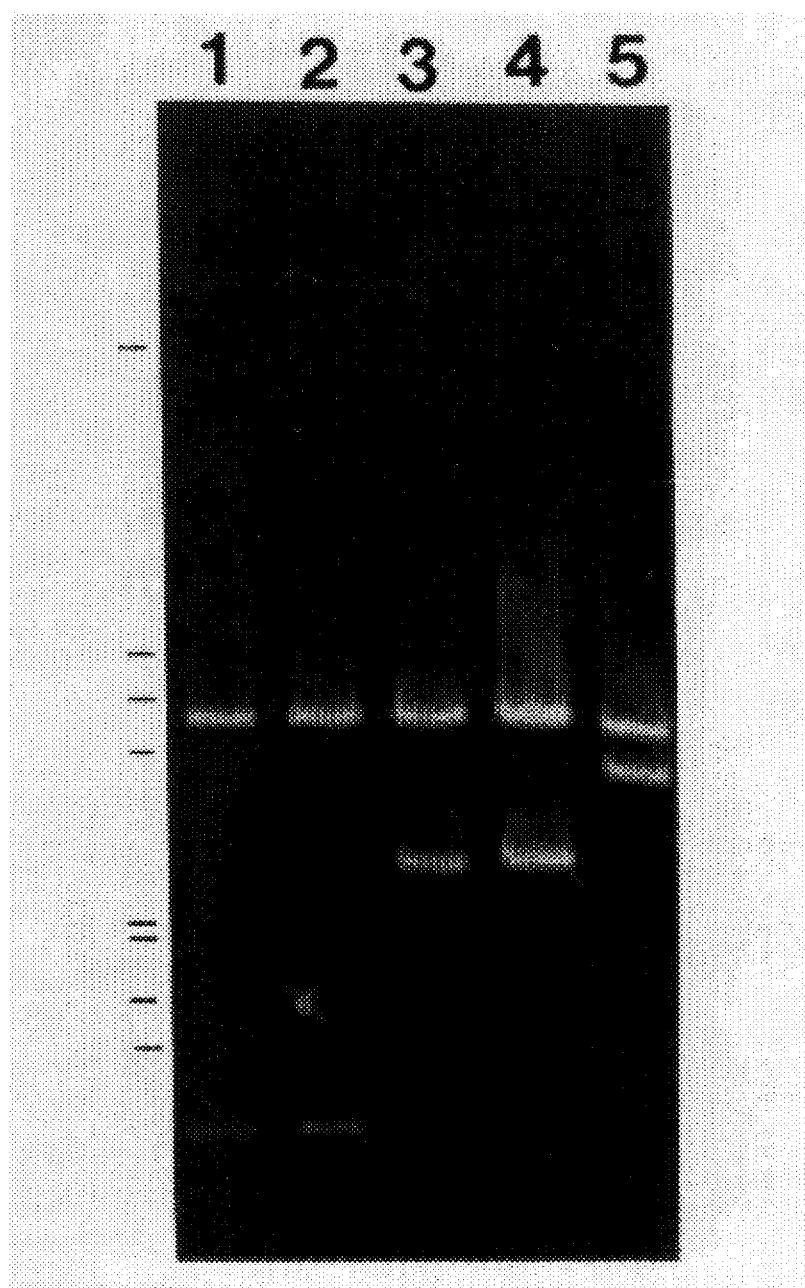
FIG. 3. A BstXI restriction digest of plasmid DNA from clones JB2a (lane 1), AH10 (lane 2), AH5 (lane 3), JB48 (lane 4), and 806-2 (lane 5) is shown. The approximate size of the DNA standards indicated are 20, 5.0, 3.5, 2.0, 1.9, 1.6, and 1.3 kilobases.
Figure 5A:
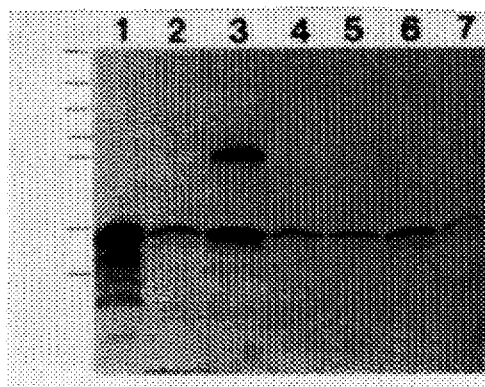
FIG. 5. Western immunoblot analysis of concentrated LB broth culture supernatants (Panels A and B) or cell extracts (Panels C and D) of *E. coli* probed with anti-beta antiserum (Panels A and C) or biotin-labelled myeloma IgA kappa (Panels B and D) are shown. Lanes 1 through 7 correspond to *E. coli* INVaF′ harboring plasmids pJB2a, AH5, 806-2, pAH10, pJB48, p618-12, or pCR™II, respectively. Clones JB2a, 806-2, AH10, 618-12, and 618-18 all contain the GBS promoter DNA for the beta antigen gene and detectable levels of beta antigen expression are consistently observed for these clones.
Figure 5B:
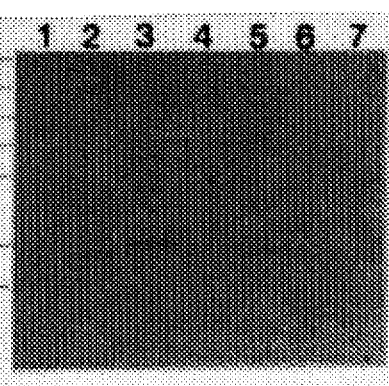
Figure 5C:
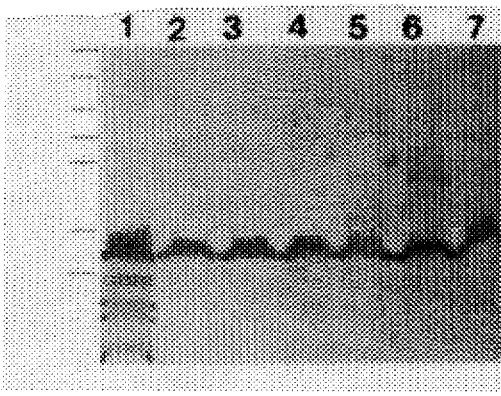
Figure 5D:
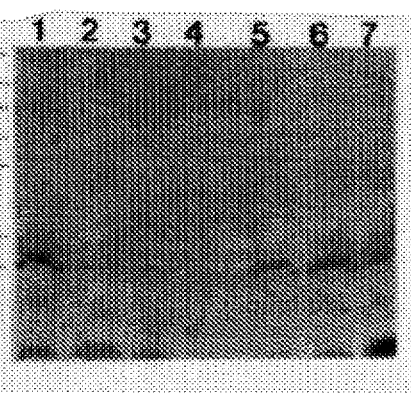

Plasmids were purified from the seven selected clones using an alkaline lysis/PEG precipitation procedure. FIG. 3 shows each plasmid (except p618-12 and p618-18) digested with BstXI to separate the insert DNA from the vector DNA.

The pCR™II vector contains 3,932 base pairs and has a BstXI site approximate 20 base pairs upstream and downstream of the TA cloning site. There are no BstXI sites within the beta antigen gene based on the two published sequences (Jerlstrom et al., 1991; Heden et al., 1991) (SEQ ID NOS. 1 and 8, respectively). All plasmids show an ≈3.9 kb fragment which represents the linear vector, and either an ≈0.95 kb, ≈2.4 kb, or ≈3.3 kb fragment which represents cloned GBS DNA.

This figure shows that identical and appropriate sized fragments were generated by PCR using oligonucleotide primers a (SEQ ID NO. 3) and b (SEQ ID. NO. 4) (lanes 1 and 2) or c (SEQ ID NO. 5) and d (SEQ ID NO. 6) (lanes 3 and 4) for both strains HG806 (lanes 1 and 3) and ss618C (lanes 2 and 4) and were successfully cloned in the pCR™II vector. The successful ligation of the ≈0.95 kb and ≈2.4 kb PCR generated DNAs to create an ≈3.3 kb beta antigen gene insert is shown for the strain HG806 derived clone, 806-2, in lane 5. Identical results were observed when p618-12 and p618-18 were digested with BstXI.

For additional confirmation that the GBS DNA contained within the clones was representative of the published beta antigen gene sequences, each plasmid was analyzed using a panel of restriction endonucleases. The predicted approximate fragments sizes, based on the published sequences of the pCR™II vector and the beta antigen gene, are listed in parentheses after each enzyme name. pJB2a and pAH10 were digested with KpnI (≈4.9 kb), BglII (≈1.7 and ≈3.2 kb), AlwNI (≈2.3 and ≈2.5 kb), XmnI (≈2.4, ≈0.5, and ≈2.0 kb), and ClaI/BssHII (≈1.7 and ≈3.2 kb). pAH5 and pJB48 were digested with KpnI (≈6.3 kb), DraIII (≈1.9, ≈0.07, and ≈4.3 kb), AlwNI (≈2.3, ≈2.5, and ≈1.5 kb), and HindIII (≈0.02, ≈0.02, ≈0.08, and ≈5.5 kb). p806-12, p618-12, and p618-18 were digested with KpnI (≈7.3 kb), BglI (≈2.3 and ≈5.0 kb), BglII (≈1.7 and ≈5.6 kb), AlwNI (≈2.3, ≈1.5, and ≈3.4 kb), and ClaI/BssHII (≈1.7 and ≈5.5 kb). The predicted digestion pattern was demonstrated in each case.

EXAMPLE 5

Sequencing of GBS Insert DNA from Plasmid JB2a

In addition to restriction endonuclease analysis, one of the clones (JB2a), harboring DNA derived from GBS strain HG806, was subjected to DNA sequence analysis. Forward and reverse M13 sequencing primers were employed as these sequences are engineered into the pCR™II cloning vector. The DNA sequence of the JB2a insert DNA (SEQ ID NO. 7) is shown in FIGS. 4A–4E. This sequence is shown aligned to the corresponding regions of the two previously-published beta antigen gene sequences (Jerlstrom et at, 1991; Heden et at, 1991) (SEQ ID NOS. 1 and 8, respectively).

EXAMPLE 6

Analysis of Clones for Beta Antigen Expression and IgA Fc Binding Activity

Cell extracts (boiling preps) and concentrated culture supernatants from each of the seven clones were tested for reactivity with rabbit anti-beta antiserum and biotin-labelled human myeloma IgA kappa by Western immunoblot analysis. Samples prepared using *E. coli* harboring only pCR™II vector DNA were included in these experiments as negative controls. The results (excluding p618-18) are shown in FIG. 5. Molecules reactive with anti-beta antibodies were seen in the culture supernatants (Panel A) of clones JB2a (lane 1)

and 806-2 (lane 3), and in the cell extracts (Panel C) of clones JB2a (lane 1), AH10 (lane 4), and 618-12 (lane 6). There was no IgA Fc binding activity observed for any of the polypeptides that reacted specifically with the anti-beta antibodies (Panels B and D). Although some non-specific IgA binding activity was observed in *E. coli* culture supernatants and cell extracts, the pattern of reactivity was the same in the test samples as the pCR™II negative control (lane 7) and hence cannot be attributed to the beta antigen. The pattern of reactivity observed for clone 618-18 is similar to that demonstrated for 618-12.

EXAMPLE 7

Vaccines

The novel beta antigen polypeptide described herein can be used advantageously in an immunogenic composition such as a vaccine. Such a composition, when administered to a person or animal, raises antibodies or other immune responses which reduce the susceptibility of that human or animal to GBS infection.

Vaccines comprising the beta antigen polypeptide disclosed herein, and variants thereof having antigenic or immunogenic properties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used. In the case of peptides, coupling to larger molecules such as KLH or tetanus toxoid sometimes enhances immunogenicity. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The compounds can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered can depend on the subject to be treated and the degree of protection desired. Advantageously, methods known to promote mucosal immunity can be combined with systemic immunity promoters to maximize protection against GBS. Also, the beta antigen polypeptide of the subject invention may be combined with carbohydrate antigenic components to enhance the immunogenic response and provide a broader range of protection. The combination may be, for example, through chemical coupling. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

Advantageously, the vaccines of the subject invention can be formulated and administered in a manner designed specifically to induce mucosal immunity.

It should be understood that the examples and embodiments described herein are for illustrative purposes only and that various modifications or changes in light thereof will be suggested to persons skilled in the art and are to be included within the spirit and purview of this application and the scope of the appended claims.

References

Anthony, B. F., N. F. Concepcion, S. M. Puentes, N. R. Payne (1990) "Nonimmune binding of human immunoglobulin A to type II group B streptococcus," *Infect. Immun.* 58:1789–1795.

Baker, C. J., (1990) "Immunization to prevent group B streptococcal disease: Victories and vexations," *J. Infect. Dis.* 161:917–921.

Baker, C. J., M. S. Edwards, D. L. Kaspar (1978) "Immunogenicity of polysaccharides from type II, group B streptococci," *J. Clin. Invest.* 61:1107–1110.

Brady, L. J., U. D. Daphtary, E. Ayoub, M. D. P. Boyle (1988) "Two novel antigens associated with group B streptococci identified by a rapid two-stage radioimmunoassay," *J. Infect. Dis.* 158:965–9772.

Brady, L. J., M. D. P. Boyle (1989) "Identification of non-immunoglobulin A Fc binding forms and low molecular weight secreted forms of the group B streptococcal beta antigen," *Infect. Immun.* 57:1573–1581.

Chun, C. S. Y., L. J. Brady, M. D. P. Boyle, H. C. Dillon, E. M. Ayoub (1991) "Group B streptococcal C proteinassociated antigens: association with neonatal sepsis," *J. Infect. Dis.* 163:786–791.

Cleat, P. H., K. N. Timmis (1987) "Cloning an expression in *Escherichia coli* of the Ibc protein genes of group B streptococci: Binding of human immunoglobulin A to the beta antigen," *Infect. Immun.* 55:1151–1155.

Coleman, R. T., D. N. Sherer, W. M. Maniscalco (1992) "Prevention of neonatal group B streptococcal infections: Advances in maternal vaccine development," *Obstetrics and Gynecology* 80:301–309.

Committee of Issues and Priorities for New Vaccine Development, Institute of Medicine (1985) "Comparisons of disease burdens and costs, and prospects for immunizing against streptococcal group B," In *New Vaccine Development: Establishing Priorities. Vol. 1. Diseases of importance in the United States.* Washington, D.C.: National Academy press, pp. 39–58 and 424–439.

Dillon, H. C., S. Khare, B. M. Gray (1987) "Group B streptococcal carriage and disease: a six-year prospective study," *J Pediatr.* 110:31–36.

Fisher, G., R. E. Horton, R. Edelman (1983) "From the National Institute of Allergy and Infectious Diseases: Summary of the National Institutes of Health workshop on group B streptococcal infection," *J. Infect. Dis.* 148:163–166.

Heden, L.-O., E. Frithz, G. Lindahl (1991) "Molecular characterization of an IgA receptor from group B streptococci: sequence of the gene, identification of a proline-rich region with unique structure and isolation of N-terminal fragments with IgA-binding capacity," *Eur. J. Immunol.* 21:1481–1490.

Jerlstron, P. G., G. S. Chatwall, K. N. Timmis (1991) "The IgA binding antigen of the C protein complex of group B streptococci: sequence determination of its gene and detection of two binding regions," *Mol. Microbiol.* 5:843–849.

Lindahl, G., B. Akerstrom, J.-P. Vaerman, L. Stenber (1990) "Characterization of an IgA receptor from group B streptococci: specificity for serum IgA," *Eur. J. Immuno* 20:2241–2247.

Kvam, A. L, O.-J. Iverson, L. Bevenger (1992) "Binding of human IgA to HCi-extracted C protein from group B streptococcus (GBS)," *APMIS* 100:1129–1132.

Madoff, L. C., J. L Michel, E. W. Gong, A. K. Rodewald, D. L. Kaspar (1992) "Protection of neonatal mice from group B streptococcal infection by maternal immunization with beta C protein," *Infect. Immun.* 60:4989–4994.

Michel, J. L., L. C. Madoff, D. E. Kling, D. L. Kaspar, F. M. Ausubel (1991) "Cloned alpha and beta C protein antigens of group B streptococci elicit protective immunity," *Infect. Immun.* 59:2023–2028.

Michel, J. L., L. C. Madoff, K. Olson, D. E. Kling, D. L. Kaspar, F. M. Ausubel (1992) "Large, identical, tandem-repeating units in the C protein alpha antigen gene, bca, of group B streptococci," *Proc. Natl. Acad. Sci. USA* 89:10060–10064.

Paoletti, L. C., M. R. Wessels, F. Michon, J. DiFabio, H. J. Jennings, D. L. Kaspar (1992) "Group B streptococcus type II polysaccharide-tetanus toxoid conjugate vaccine," *Infect. Immun.* 60:4009–4014.

Rainard, P. (1992) "Isotype antibody response in cows to *Streptococcus agalactiae* group B polysaccharide-ovalbumin conjugate," *J. Clin.. Microbiol.* 30:1856–1862.

Russell-Jones, G. J., E. C. Gotschlich (1984) "Identification of protein antigens of group B streptococci with special reference to the Ibc antigens," *J. Exp. Med,* 160:1476–1484.

Russell-Jones, G. J., E. C. Gotschlich, M. S. Blake (1984) "A surface receptor specific for human IgA on group B streptococci possessing the Ibc protein antigen," *J. Exp. Med.* 160:1467–1475.

Wessels, M. R., L. C. Paoletti, D. L. Kaspar, J. L. Fabio, F. Michon, K. Holme, H. J. Jennings (1990) "Immunogenicity in animals of a polysaccharide-protein conjugate vaccine against type III group B streptococcus," *J. Chin. Invest.* 86:1429–1433.

Wessels, M. R., L. C. Paoletti, A. K. Rodewald, F. Michon, J. DiFabio, H. J. Jennings, D. L. Kaspar (1993) "Stimulation of protective antibodies against Ia and Ib group B streptococci by a type Ia polysaccharide-tetanus toxoid conjugate vaccine." *Infect. Immun.* 61:4760–4766.

---

I claim:

1. A purified polynucleotide molecule, comprising a nucleotide sequence that encodes a mutant beta antigen polypeptide from group B streptococci, or a fragment thereof, wherein said polypeptide is immunoreactive with anti-beta antigen antiserum and comprises the amino terminus region of the wild the beta antigen, and wherein said polypeptide does not bind to the Fc region of human IgA immunoglobulin, with the proviso that said polypeptide is not the approximately 38kD polypeptide secreted by the group B streptococcus strain HG 806.

2. A purified mutant beta antigen polypeptide from group B streptococci coded for by the polynucleotide molecule of claim 1.

3. An immunogenic composition comprising the beta antigen polypeptide of claim 2 in a pharmacologically-acceptable vehicle.

4. A method of raising antibodies to a group B streptococcus, said method comprising the administration of an effective amount of a composition comprising the beta antigen polypeptide of claim 2 to a human or animal in a pharmacologically-acceptable vehicle.

5. A recombinant polynucleotide transfer vector comprising a polynucleotide cloning vehicle and the polynucleotide molecule of claim 1.

6. A host cell transformed by the recombinant polynucleotide transfer vector of claim 5.

* * * * *

UNITED STATES PATENT AND TRADEMARK OFFICE
CERTIFICATE OF CORRECTION

PATENT NO. : 5,766,606

ISSUED : June 16, 1998

INVENTOR(S) : L. Jeannine Brady

It is certified that error appears in the above-identified patent and that said Letters Patent is hereby corrected as shown below:

Column 1, line 50: "m organisms," should read --III organisms,--.

Column 3, line 4: "INVaF' " should read --INV$\alpha$F'--.

Column 6, line 29: "INVaF' " should read --INV$\alpha$F'--;

line 51: "Callif.)" should read --CA)--; and line 67: "(PD$\approx$ 10" should read --(PD-10--.

Column 8, line 21: "40 yl" should read --40 $\mu$l--;

line 48: "(SEQ ID NO. 11)" should read --(SEQ ID NO. 4)--; and line 50: "restriction 5 sequences" should read --restriction sequences--.

Column 10, line 10: "INVaF' " should read --INV$\alpha$F'--; and line 17: "p816-2" should read --p806-2--.

Column 11, line 26: "DraII" should read --DraIII--; and line 27: "KnI" should read --KpnI--.

Column 13, line 18: "INVaF' " should read --INV$\alpha$F'--.

Column 17, line 10: "J Pediatr." should read --J. Pediatr.--.

UNITED STATES PATENT AND TRADEMARK OFFICE
CERTIFICATE OF CORRECTION

Page 2 of 2

PATENT NO.  :  5,766,606

ISSUED  :  June 16, 1998

INVENTOR(S)  :  L. Jeannine Brady

It is certified that error appears in the above-identified patent and that said Letters Patent is hereby corrected as shown below:

Column 17, line 28: "Immuno" should read --Immunol.--; and line 31: "Hci" should read --HCl--.

Column 18, line 21: "Med," should read --Med.--;

line 27: "J. L. Fabio" should read --J. L. DiFabio--; and line 30: "J. Chin." should read --J. Clin.--.

Column 33, line 17, Claim 1: "wild the" should read --wild type--.

Signed and Sealed this

Fifth Day of January, 1999

*Attest:*

*Attesting Officer*     *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4200 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AAGCTTATGC  TTGTCAATAA  TCACAAATTT  GTAGATCACT  TCCTTTTTAG  GACTGTAAAG       60

CATCCTAATT  ACTTTTTAAA  TATATTACCA  GAACTAGTTG  GTTTGGCCCT  GGTGAGTCAT      120

GCTTATGTGA  CATTCATCTT  TATTTTTCCT  GTCTATGCGG  TTATTCTTTA  TCAAAGAATA      180

GCAGAGGAAG  AAAAATTATT  GCAGGAAGTT  ATTATTCCGA  ATGGAAGAAT  GAAAGGTTAA      240

AAATAATATA  CCCAATTTAA  TATGCAGTTC  ATATTGGAAG  GGTATACTGT  AGATAAATAA      300

AATATTGGAG  GATATCGATA  TGTTTAAATC  TAATTATGAA  AGAAAAATGC  GTTATTCCAT      360

TCGTAAATTT  AGTGTAGGAG  TAGCTAGTGT  AGCGGTAGCT  AGTTTGTTCA  TGGGAAGCGT      420
```

-continued

| | | | | | |
|---|---|---|---|---|---|
| TGCTCATGCA | AGTGAGCTTG | TAAAGGACGA | TAGTGTGAAG | ACTACCGAGG | TTGCAGCTAA | 480 |
| GCCCTATCCA | AGTATGGCTC | AAACAGATCA | AGGAAATAAT | TCATCATCCT | CGGAACTTGA | 540 |
| GACAACAAAG | ATGGAAATTC | CTACAACAGA | CATAAAAAAA | GCTGTTGAAC | CGGTCGAGAA | 600 |
| AACAGCTGGG | GAAACATCTG | CCACTGATAC | TGGAAAACGA | GAGAACAAT | TACAACAATG | 660 |
| GAAAATAAT | CTAAAAAATG | ATGTGGATAA | CACAATTCTA | TCTCATGAAC | AGAAAAATGA | 720 |
| GTTAAAACA | AAAATTGATG | AAACAAATGA | TTCTGATGCA | TTATTAGAAT | TAGAAAATCA | 780 |
| ATTTAACGAA | ACTAATAGAC | TGTTACACAT | CAAACAACAT | GAAGAAGTTG | AGAAAGATAA | 840 |
| GAAAGCTAAG | CAACAGAAAA | CTCTGAAACA | GTCAGATACG | AAAGTAGATC | TAAGCAATAT | 900 |
| TGACAAAGAG | CTTAATCATC | AAAAAAGTCA | AGTTGAAAAA | ATGGCAGAGC | AAAAGGGAAT | 960 |
| CACAAATGAA | GATAAAGATT | CTATGCTGAA | AAAAATCGAA | GATATTCGTA | ACAAGCTCA | 1020 |
| ACAAGCAGAT | AAAAAGAAG | ATGCCGAAGT | AAAGGTTCGT | GAAGAACTAG | GTAAACTCTT | 1080 |
| TAGTTCAACT | AAAGCTGGTC | TGGATCAAGA | AATTCAAGAG | CATGTGAAGA | AAGAAACGAG | 1140 |
| TAGTGAGGAA | AATACTCAGA | AAGTTGATGA | ACACTATGCT | AATAGCCTTC | AGAACCTTGC | 1200 |
| TCAAAAATCT | CTTGAAGAAC | TAGATAAGGC | AACTACCAAT | GAACAAGCTA | CACAAGTTAA | 1260 |
| AAATCAATTC | TTAGAAAACG | CTCAAAAGCT | CAAAGAAATA | CAACCTCTTA | TCAAAGAAAC | 1320 |
| GAATGTGAAA | TTGTATAAGG | CTATGAGTGA | GAGCTTGGAG | CAGGTTGAGA | AGGAATTAAA | 1380 |
| ACATAATTCG | GAAGCTAATT | TAGAAGATTT | GGTTGCGAAA | TCTAAAGAAA | TCGTAAGAGA | 1440 |
| ATACGAAGGA | AAACTTAATC | AATCTAAAAA | TCTTCCAGAA | TTAAAGCAAC | TAGAAGAGGA | 1500 |
| AGCTCATTCG | AAGTTGAAAC | AAGTTGTGGA | GGATTTTAGA | AAAAAATTTA | AACGTCAGA | 1560 |
| GCAAGTGACA | CCAAAAAAAC | GTGTCAAACG | AGATTTAGCT | GCTAATGAAA | ATAATCAACA | 1620 |
| AAAGATTGAG | TTAACAGTTT | CACCAGAGAA | TATCACTGTA | TATGAAGGTG | AAGACGTGAA | 1680 |
| ATTTACAGTC | ACAGCTAAAA | GTGATTCGAA | GACGACGTTG | GACTTCAGTG | ATCTTTTAAC | 1740 |
| AAAATATAAT | CCGTCTGTAT | CAGATAGAAT | TAGTACAAAT | TATAAGACTA | ACACGGATAA | 1800 |
| TCATAAGATT | GCCGAAATCA | CTATCAAGAA | TTTGAAGCTA | AATGAAAGTC | AAACAGTGAC | 1860 |
| TCTAAAAGCT | AAAGATGATT | CTGGCAATGT | AGTTGAAAAA | ACATTCACTA | TTACAGTGCA | 1920 |
| AAAGAAAGAG | GAGAAACAAG | TTCCTAAAAC | ACCAGAGCAG | AAAGATTCTA | AACGGAAGA | 1980 |
| AAAGGTTCCT | CAAGAACCAA | AATCAAATGA | CAAGAATCAA | TTACAAGAGT | TGATTAAATC | 2040 |
| AGCTCAACAA | GAACTGGAAA | AGTTAGAAAA | AGCAATAAAA | GAATTAATGG | AGCAACCAGA | 2100 |
| GATTCCATCC | AATCCAGAGT | ATGGTATTCA | AAAATCTATT | TGGGAGTCAC | AAAAAGAGCC | 2160 |
| TATCCAGGAA | GCCATAACAA | GTTTTAAGAA | GATTATTGGT | GATTCATCTT | CAAAATACTA | 2220 |
| CACAGAGCAC | TATTTTAACA | AATATAAATC | TGATTTTATG | AATTATCAAC | TTCATGCACA | 2280 |
| AATGGAGATG | CTGACTAGAA | AAGTGGTTCA | GTATATGAAC | AAATATCCTG | ATAATGCAGA | 2340 |
| AATTAAAAAG | ATATTTGAGT | CAGATATGAA | GAGAACGAAA | GAAGATAATT | ACGGAAGTTT | 2400 |
| AGAAAATGAT | GCTTTGAAAG | GCTATTTTGA | GAAATATTTC | CTTACACCAT | TTAATAAAAT | 2460 |
| TAAGCAGATT | GTAGATGATT | TGGATAAAAA | AGTAGAACAA | GATCAGCCAG | CACCAATTCC | 2520 |
| GGAAAATTCA | GAAATGGATC | AGGCTAAGGA | AAAGGCTAAG | ATTGCTGTAT | CGAAGTATAT | 2580 |
| GAGTAAGGTT | TTAGATGGAG | TTCATCAACA | TCTGCAGAAG | AAAAATAACA | GTAAAATTGT | 2640 |
| TGATCTTTTT | AAGGAACTTG | AAGCGATTAA | ACAACAAACT | ATTTTTGATA | TTGACAATGC | 2700 |
| AAAGACTGAA | GTAGAGATTG | ATAACTTAGT | ACACGATGCA | TTCTCAAAAA | TGAATGCTAC | 2760 |
| TGTTGCTAAA | TTTCAAAAAG | GTCTAGAGAC | AAATACGCCA | GAAACTCCAG | ATACACCGAA | 2820 |

-continued

| | | | | | |
|---|---|---|---|---|---|
| GATTCCAGAG | CTACCTCAAG | CCCCAGATAC | ACCGCAGGCT | CCAGACACAC | CGCATGTTCC | 2880 |
| GGAATCACCA | AAGGCCCCAG | AAGCACCGCG | TGTTCCGGAA | TCACCAAAGA | CTCCAGAAGC | 2940 |
| ACCGCATGTT | CCGGAATCAC | CAAAGGCCCC | AGAAGCACCG | CGTGTTCCGG | AATCACCAAA | 3000 |
| GACTCCAGAA | GCACCGCATG | TTCCGGAATC | ACCAAAGACT | CCAGAAGCAC | CAAAGATTCC | 3060 |
| GGAACCCCCT | AAGACTCCAG | ACGTCCCTAA | GCTTCCAGAC | GTCCCTAAGC | TTCCAGACGT | 3120 |
| CCCTAAGCTT | CCAGATGCAC | CGAAGTTACC | AGATGGGTTA | ATAAAGTTG | GACAAGCAGT | 3180 |
| ATTTACATCA | ACTGATGGAA | ATACTAAGGT | TACGGTTGTA | TTTGATAAAC | CTACAGATGC | 3240 |
| TGATAAGTTA | CATCTCAAGG | AAGTAACGAC | GAAAGAGTTG | GCTGATAAAA | TTGCTCATAA | 3300 |
| AACAGGAGGA | GGAACAGTTC | GTGTGTTTGA | CTTATCTCTT | TCTAAAGGAG | GCAAGGAAAC | 3360 |
| ACATGTCAAT | GGAGAACGAA | CTGTTCGGCT | CGCGCTTGGG | CAGACTGGCT | CAGATGTTCA | 3420 |
| CGTCTATCAC | GTAAAGGAAA | ATGGCGACCT | TGAGCGTATT | CCTTCTAAAG | TTGAAAATGG | 3480 |
| GCAAGTTGTT | TTTAAAACGA | ACCACTTCAG | TTTGTTGCG | ATTAAGACAC | TTTCTAAGGA | 3540 |
| TCAAAATGTT | ACTCCACCGA | AGCAGACTAA | ACCTTCTACC | CAAGGCAGTC | AAGTAGAGAT | 3600 |
| TGCAGAGAGT | CAAACTGGAA | AATTCCAGAG | TAAAGCAGCT | AATCATAAAG | CACTGGCTAC | 3660 |
| TGGAAATGAA | ACAGTGGCAA | AAGGAAATCC | TACATCAACA | ACGGAAAAGA | AATTGCCATA | 3720 |
| TACAGGAGTG | GCATCTAATC | TAGTTCTTGA | AATTATGGGT | CTCCTTGGTT | TGATTGGAAC | 3780 |
| TTCATTCATC | GCAATGAAAA | GAAGAAAATC | ATGATTCAGT | TTTTAAAAA | TATCCACTTT | 3840 |
| CGATATCTAG | CATTTGATTG | GTTATCTGTG | GATGATTCTA | AAGATGTTAC | CTATCGTTGG | 3900 |
| TATGTAACAA | TTATAAGTCA | TTTCATATAA | AAGAGGCTCT | TTGTCAACTG | TAGTTGGTTG | 3960 |
| AAACAAGGCT | ACAAACTAGA | AAGGACGCAT | TTTGTCCTTT | CTTTTGATG | TTGAGGGCAA | 4020 |
| TGAAAATACG | CTTTTGAAG | TTTTCAAAAT | TCCGAAAACT | AAAGATATTG | TATTTGAAAA | 4080 |
| GTTTAATGAG | ATGATTAGTT | GCTTCCAATT | TTGCGTTGGA | GTAGGTTAC | TGAAGGACGT | 4140 |
| TGACGATATT | CTCTTTGCTT | TTGAGAATGA | TTTTAAAGAT | AGTCTGAAAA | AGAGGATGAA | 4200 |

( 2 ) INFORMATION FOR SEQ ID NO:2:

( i ) SEQUENCE CHARACTERISTICS:
        ( A ) LENGTH: 984 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser Glu Leu Val Lys Asp Asp Ser Val Lys Thr Thr Glu Val Ala Ala
 1               5                  10                  15

Lys Pro Tyr Pro Ser Met Ala Gln Thr Asp Gln Gly Asn Asn Ser Ser
            20                  25                  30

Ser Ser Glu Leu Glu Thr Thr Lys Met Glu Ile Pro Thr Thr Asp Ile
        35                  40                  45

Lys Lys Ala Val Glu Pro Val Glu Lys Thr Ala Gly Glu Thr Ser Ala
    50                  55                  60

Thr Asp Thr Gly Lys Arg Glu Lys Gln Leu Gln Gln Trp Lys Asn Asn
65                  70                  75                  80

Leu Lys Asn Asp Val Asp Asn Thr Ile Leu Ser His Glu Gln Lys Asn
                85                  90                  95

Glu Phe Lys Thr Lys Ile Asp Glu Thr Asn Asp Ser Asp Ala Leu Leu
            100                 105                 110

Glu Leu Glu Asn Gln Phe Asn Glu Thr Asn Arg Leu Leu His Ile Lys
```

|     |     |     | 115 |     |     |     | 120 |     |     |     | 125 |     |     |     |
|---|---|---|---|---|---|---|---|---|---|---|---|---|---|---|
| Gln | His | Glu | Glu | Val | Glu | Lys | Asp | Lys | Lys | Ala | Lys | Gln | Gln | Lys | Thr |
|     |     |     |     |     | 130 |     |     |     | 135 |     |     |     | 140 |     |     |
| Leu | Lys | Gln | Ser | Asp | Thr | Lys | Val | Asp | Leu | Ser | Asn | Ile | Asp | Lys | Glu |
| 145 |     |     |     |     | 150 |     |     |     | 155 |     |     |     |     |     | 160 |
| Leu | Asn | His | Gln | Lys | Ser | Gln | Val | Glu | Lys | Met | Ala | Glu | Gln | Lys | Gly |
|     |     |     |     | 165 |     |     |     |     | 170 |     |     |     |     | 175 |     |
| Ile | Thr | Asn | Glu | Asp | Lys | Asp | Ser | Met | Leu | Lys | Lys | Ile | Glu | Asp | Ile |
|     |     |     | 180 |     |     |     |     | 185 |     |     |     |     | 190 |     |     |
| Arg | Lys | Gln | Ala | Gln | Ala | Asp | Lys | Lys | Glu | Asp | Ala | Glu | Val | Lys |     |
|     |     | 195 |     |     |     | 200 |     |     |     | 205 |     |     |     |     |     |
| Val | Gln | Leu | Glu | Glu | Glu | Ala | His | Ser | Lys | Leu | Lys | Gln | Val | Val | Glu |
|     | 210 |     |     |     |     | 215 |     |     |     |     | 220 |     |     |     |     |
| Asp | Phe | Arg | Lys | Lys | Phe | Lys | Thr | Ser | Glu | Gln | Val | Thr | Pro | Lys | Lys |
| 225 |     |     |     |     | 230 |     |     |     | 235 |     |     |     |     |     | 240 |
| Arg | Val | Lys | Arg | Asp | Leu | Ala | Ala | Asn | Glu | Asn | Asn | Gln | Gln | Lys | Ile |
|     |     |     |     | 245 |     |     |     | 250 |     |     |     | 255 |     |     |     |
| Glu | Leu | Thr | Val | Ser | Pro | Glu | Asn | Ile | Thr | Val | Tyr | Glu | Gly | Glu | Asp |
|     |     |     | 260 |     |     |     | 265 |     |     |     |     | 270 |     |     |     |
| Val | Lys | Phe | Thr | Val | Thr | Ala | Lys | Ser | Asp | Ser | Lys | Thr | Thr | Leu | Asp |
|     |     | 275 |     |     |     |     | 280 |     |     |     | 285 |     |     |     |     |
| Phe | Ser | Asp | Leu | Leu | Thr | Lys | Tyr | Asn | Pro | Ser | Val | Ser | Asp | Arg | Ile |
|     | 290 |     |     |     |     | 295 |     |     |     | 300 |     |     |     |     |     |
| Ser | Thr | Asn | Tyr | Lys | Thr | Asn | Thr | Asp | Asn | His | Lys | Ile | Ala | Glu | Ile |
| 305 |     |     |     |     | 310 |     |     |     | 315 |     |     |     |     |     | 320 |
| Thr | Ile | Lys | Asn | Leu | Lys | Leu | Asn | Glu | Ser | Gln | Thr | Val | Thr | Leu | Lys |
|     |     |     |     | 325 |     |     |     | 330 |     |     |     |     | 335 |     |     |
| Ala | Lys | Asp | Asp | Ser | Gly | Asn | Val | Val | Glu | Lys | Thr | Phe | Thr | Ile | Thr |
|     |     |     | 340 |     |     |     | 345 |     |     |     |     | 350 |     |     |     |
| Val | Gln | Lys | Lys | Glu | Glu | Lys | Gln | Val | Pro | Lys | Thr | Pro | Glu | Gln | Lys |
|     | 355 |     |     |     |     | 360 |     |     |     |     | 365 |     |     |     |     |
| Asp | Ser | Lys | Thr | Glu | Glu | Lys | Val | Pro | Gln | Glu | Pro | Lys | Ser | Asn | Asp |
|     | 370 |     |     |     |     | 375 |     |     |     | 380 |     |     |     |     |     |
| Lys | Asn | Gln | Leu | Gln | Glu | Leu | Ile | Lys | Ser | Ala | Gln | Gln | Glu | Leu | Glu |
| 385 |     |     |     |     | 390 |     |     |     | 395 |     |     |     |     |     | 400 |
| Lys | Leu | Glu | Lys | Ala | Ile | Lys | Glu | Leu | Met | Glu | Gln | Pro | Glu | Ile | Pro |
|     |     |     |     | 405 |     |     |     | 410 |     |     |     |     | 415 |     |     |
| Ser | Asn | Pro | Glu | Tyr | Gly | Ile | Gln | Lys | Ser | Ile | Trp | Glu | Ser | Gln | Lys |
|     |     |     | 420 |     |     |     | 425 |     |     |     | 430 |     |     |     |     |
| Glu | Pro | Ile | Gln | Glu | Ala | Ile | Thr | Ser | Phe | Lys | Lys | Ile | Ile | Gly | Asp |
|     |     | 435 |     |     |     |     | 440 |     |     |     |     | 445 |     |     |     |
| Ser | Ser | Ser | Lys | Tyr | Tyr | Thr | Glu | His | Tyr | Phe | Asn | Lys | Tyr | Lys | Ser |
|     | 450 |     |     |     |     | 455 |     |     |     | 460 |     |     |     |     |     |
| Asp | Phe | Met | Asn | Tyr | Gln | Leu | His | Ala | Gln | Met | Glu | Met | Leu | Thr | Arg |
| 465 |     |     |     | 470 |     |     |     | 475 |     |     |     |     |     |     | 480 |
| Lys | Val | Val | Gln | Tyr | Met | Asn | Lys | Tyr | Pro | Asp | Asn | Ala | Glu | Ile | Lys |
|     |     |     | 485 |     |     |     | 490 |     |     |     |     |     |     | 495 |     |
| Lys | Ile | Phe | Glu | Ser | Asp | Met | Lys | Arg | Thr | Lys | Glu | Asp | Asn | Tyr | Gly |
|     |     |     | 500 |     |     |     | 505 |     |     |     |     | 510 |     |     |     |
| Ser | Leu | Glu | Asn | Asp | Ala | Leu | Lys | Gly | Tyr | Phe | Glu | Lys | Tyr | Phe | Leu |
|     |     |     | 515 |     |     |     | 520 |     |     |     | 525 |     |     |     |     |
| Thr | Pro | Phe | Asn | Lys | Ile | Lys | Gln | Ile | Val | Asp | Asp | Leu | Asp | Lys | Lys |
|     |     | 530 |     |     |     | 535 |     |     |     | 540 |     |     |     |     |     |

| | | | | | | | | | | | | | | |
|---|---|---|---|---|---|---|---|---|---|---|---|---|---|---|
|Val|Glu|Gln|Asp|Gln|Pro|Ala|Pro|Ile|Pro|Glu|Asn|Ser|Glu|Met|Asp|
|545| | | | |550| | | |555| | | | |560|
|Gln|Ala|Lys|Glu|Lys|Ala|Lys|Ile|Ala|Val|Ser|Lys|Tyr|Met|Ser|Lys|
| | | | |565| | | |570| | | | |575| | |
|Val|Leu|Asp|Gly|Val|His|Gln|His|Leu|Gln|Lys|Lys|Asn|Asn|Ser|Lys|
| | | |580| | | |585| | | | |590| | | |
|Ile|Val|Asp|Leu|Phe|Lys|Glu|Leu|Glu|Ala|Ile|Lys|Gln|Gln|Thr|Ile|
| | |595| | | |600| | | |605| | | | | |
|Phe|Asp|Ile|Asp|Asn|Ala|Lys|Thr|Glu|Val|Glu|Ile|Asp|Asn|Leu|Val|
| |610| | | |615| | | |620| | | | | | |
|His|Asp|Ala|Phe|Ser|Lys|Met|Asn|Ala|Thr|Val|Ala|Lys|Phe|Gln|Lys|
|625| | | |630| | | |635| | | | | | |640|
|Gly|Leu|Glu|Thr|Asn|Thr|Pro|Glu|Thr|Pro|Asp|Thr|Pro|Lys|Ile|Pro|
| | | |645| | | |650| | | | |655| | | |
|Glu|Leu|Pro|Gln|Ala|Pro|Asp|Thr|Pro|Gln|Ala|Pro|Asp|Thr|Pro|His|
| | | |660| | | |665| | | | |670| | | |
|Val|Pro|Glu|Ser|Pro|Lys|Ala|Pro|Glu|Ala|Pro|Arg|Val|Pro|Glu|Ser|
| | |675| | | |680| | | |685| | | | | |
|Pro|Lys|Thr|Pro|Glu|Ala|Pro|His|Val|Pro|Glu|Ser|Pro|Lys|Ala|Pro|
| |690| | | |695| | | |700| | | | | | |
|Glu|Ala|Pro|Arg|Val|Pro|Glu|Ser|Pro|Lys|Thr|Pro|Glu|Ala|Pro|His|
|705| | | |710| | | |715| | | | | | |720|
|Val|Pro|Glu|Ser|Pro|Lys|Thr|Pro|Glu|Ala|Pro|Lys|Ile|Pro|Glu|Pro|
| | | |725| | | |730| | | | |735| | | |
|Pro|Lys|Thr|Pro|Asp|Val|Pro|Lys|Leu|Pro|Asp|Val|Pro|Lys|Leu|Pro|
| | |740| | | |745| | | | |750| | | | |
|Asp|Val|Pro|Lys|Leu|Pro|Asp|Ala|Pro|Lys|Leu|Pro|Asp|Gly|Leu|Asn|
| | |755| | | |760| | | |765| | | | | |
|Lys|Val|Gly|Gln|Ala|Val|Phe|Thr|Ser|Thr|Asp|Gly|Asn|Thr|Lys|Val|
| |770| | | |775| | | |780| | | | | | |
|Thr|Val|Val|Phe|Asp|Lys|Pro|Thr|Asp|Ala|Asp|Lys|Leu|His|Leu|Lys|
|785| | | |790| | | |795| | | | | | |800|
|Glu|Val|Thr|Thr|Lys|Glu|Leu|Ala|Asp|Lys|Ile|Ala|His|Lys|Thr|Gly|
| | | |805| | | |810| | | | |815| | | |
|Gly|Gly|Thr|Val|Arg|Val|Phe|Asp|Leu|Ser|Leu|Ser|Lys|Gly|Gly|Lys|
| | |820| | | |825| | | |830| | | | | |
|Glu|Thr|His|Val|Asn|Gly|Glu|Arg|Thr|Val|Arg|Leu|Ala|Leu|Gly|Gln|
| | |835| | | |840| | | |845| | | | | |
|Thr|Gly|Ser|Asp|Val|His|Val|Tyr|His|Val|Lys|Glu|Asn|Gly|Asp|Leu|
| |850| | | |855| | | |860| | | | | | |
|Glu|Arg|Ile|Pro|Ser|Lys|Val|Glu|Asn|Gly|Gln|Val|Val|Phe|Lys|Thr|
|865| | | |870| | | |875| | | | | | |880|
|Asn|His|Phe|Ser|Leu|Phe|Ala|Ile|Lys|Thr|Leu|Ser|Lys|Asp|Gln|Asn|
| | | |885| | | |890| | | | |895| | | |
|Val|Thr|Pro|Pro|Lys|Gln|Thr|Lys|Pro|Ser|Thr|Gln|Gly|Ser|Gln|Val|
| | |900| | | |905| | | | |910| | | | |
|Glu|Ile|Ala|Glu|Ser|Gln|Thr|Gly|Lys|Phe|Gln|Ser|Lys|Ala|Ala|Asn|
| | |915| | | |920| | | | |925| | | | |
|His|Lys|Ala|Leu|Ala|Thr|Gly|Asn|Glu|Thr|Val|Ala|Lys|Gly|Asn|Pro|
| |930| | | |935| | | |940| | | | | | |
|Thr|Ser|Thr|Thr|Glu|Lys|Lys|Leu|Pro|Tyr|Thr|Gly|Val|Ala|Ser|Asn|
|945| | | |950| | | |955| | | | | | |960|
|Leu|Val|Leu|Glu|Ile|Met|Gly|Leu|Leu|Gly|Leu|Ile|Gly|Thr|Ser|Phe|
| | | |965| | | |970| | | | |975| | | |

```
        Ile Ala Met Lys Arg Arg Lys Ser
                    980
```

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GCGGATCCGC TTATGTGACA TTCATC                                        26
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GCGTCGACAA CCTTTACTTC GGCATC                                        26
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GCGTCGACCT AGAAGAGGAA GCTCAT                                        26
```

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GCGGATCCAT CAAATGCTAG ATATCG                                        26
```

( 2 ) INFORMATION FOR SEQ ID NO:7:

( i ) SEQUENCE CHARACTERISTICS:
        ( A ) LENGTH: 932 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
CTTATGTACA TTCATCTTTA TTTTCCTGT CTATGCGGTT ATTCTTTATC AAAGAATAGC    60
AGAGGAAGAA AAATTATTGC AGGAAGTTAT TATTCCGAAT GGAAGAATGA AAGGTTAAAA   120
```

| | | | | | |
|---|---|---|---|---|---|
| ATAATATACC | CAATTTAATA | TGCAGTTCAT | ATTGGAAGGG | TATACTGTAG | ATAAATAAAA | 180 |
| TATTGGGGAT | ATCGATATGT | TTAAATCTAA | TTATGAAAGA | AAAATGCGTT | ATTCCATTCG | 240 |
| TAAATTTAGT | GTAGGAGTAG | CTAGTGTAGC | GGTAGCTAGT | TTATTCATGG | GAAGCGTTGC | 300 |
| TCATGCAAGT | GAGCTTGTAA | AGGACGATAG | TGTGAAGACT | ACCGAGGTTG | CAGCTAAGCC | 360 |
| CTATCCAAGT | ATGGCTCAAA | CAGATCAAGG | AAATAATTCA | TCATCCTCGG | AACTTGAGAC | 420 |
| AACAAAGATG | GAAATTCCTA | CAACAGACAT | AAAAAAAGCT | GTTGAACCGG | TCGAGAAAAC | 480 |
| AGCTGGGGAA | ACATCTGCCA | CTGATACTGG | AAAACGAGAG | AAACAATTAC | AACAATGGAA | 540 |
| AAATAATCTA | AAAATGATG | TGGATAACAC | AATTCTATCT | CATGAACAGA | AAAATGAGTT | 600 |
| TAAAACAAAA | ATTGATGAAA | CAAATGATTC | TGATGCATTA | TTAGAATTAG | AAAATCAATT | 660 |
| TAACGAAACT | AATAGACTGT | TACACATCAA | ACAACATGAA | GAAGTTGAGA | AAGATAAGAA | 720 |
| AGCTAAGCAA | CAGAAAACTC | TGAAACAGTC | AGATACGAAA | GTAGATCTAA | GCAATATTGA | 780 |
| CAAAGAGCTT | AATCATCAAA | AAAGTCAAGT | TGAAAAAATG | GCAGAGCAAA | AGGGAATCAC | 840 |
| AAATGAAGAT | AAAGATCTAT | GCTGAAAAAA | ATCGAAGATA | TTCGTAAACA | AGCTCAACAA | 900 |
| GCAGATAAAA | AAGAGATGCC | GAAGTAAAGG | TT | | | 932 |

(2) INFORMATION FOR SEQ ID NO:8:

(i) SEQUENCE CHARACTERISTICS:
        (A) LENGTH: 3730 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| AAAAATTATT | GCAGGAAGTT | ATTATTCCGA | ATGGAAGAAT | GAAAGGTTAA | AAATAATATA | 60 |
| CCCAATTTAA | TATGCAGTTC | ATATTGGAAG | GGTATACTGT | AGATAAATAA | AATATTGGAG | 120 |
| GATATCGATA | TGTTTAAATC | TAATTATGAA | AGAAAAATGC | GTTATTCCAT | TCGTAAATTT | 180 |
| AGTGTAGGAG | TAGCTAGTGT | AGCGGTACGT | AGTTTGTTCA | TGGGAAGCGT | TGCTCATGCA | 240 |
| AGTGAGCTTG | TAAAGGACGA | TAGTGTGAAG | ACTACCGAGG | TTGCAGCTAA | GCCCTATCCA | 300 |
| AGTATGGCTC | AAACAGATCA | AGGAAATAAT | TCATCATCCT | CGGAACTTGA | GACAACAAAG | 360 |
| ATGGAAATTC | CTACAACAGA | CATAAAAAAA | GCTGTTGAAC | CGGTCGAGAA | AACAGCTGGG | 420 |
| GAAACATCTG | CCACTGATAC | TGGAAAACGA | GAGAACAAT | TACAACAATG | GAAAAATAAT | 480 |
| CTAAAAAATG | ATGTGGATAA | CACAATTCTA | TCTCATGAAC | AGAAAAATGA | GTTTAAAACA | 540 |
| AAAATTGATG | AAACAAATGA | TTCTGATGCA | TTATTAGAAT | TAGAAAATCA | ATTTAACGAA | 600 |
| ACTAATAGAC | TGTTACACAT | CAAACAACAT | GAAGAAGTTG | AGAAAGATAA | GAAAGCTAAG | 660 |
| CAACAGAAAA | CTCTGAAACA | GTCAGATACG | AAAGTAGATC | TAAGCAATAT | TGACAAAGAG | 720 |
| CTTAATCATC | AAAAAAGTCA | AGTTGAAAAA | ATGGCAGAGC | AAAAGGGAAT | CACAAATGAA | 780 |
| GATAAAGATT | CTATGCTGAA | AAAATCGAA | GATATTCGTA | AACAAGCTCA | ACAAGCAGAT | 840 |
| AAAAAGAAG | ATGCCGAAGT | AAAGGTTCGT | GAAGAACTAG | GTAAACTCTT | TAGTTCAACT | 900 |
| AAAGCTGGTC | TGGATCAAGA | AATTCAAGAG | CATGTGAAGA | AAGAAACGAG | TAGTGAGGAA | 960 |
| AATACTCAGA | AAGTTGATGA | ACACTATGCT | AATAGCCTTC | AGAACCTTGC | TCAAAAATCT | 1020 |
| CTTGAAGAAC | TAGATAAGGC | AACTACCAAT | GAACAAGCTA | CACAAGTTAA | AAATCAATTC | 1080 |
| TTAGAAAACG | CTCAAAAGCT | CAAAGAAATA | CAACCTCTTA | TCAAAGAAAC | GAATGTGAAA | 1140 |

| | | | | | |
|---|---|---|---|---|---|
| TTGTATAAGG | CTATGAGTGA | GAGCTTGGAG | CAGGTTGAGA | AGGAATTAAA | ACATAATTCG | 1200 |
| GAAGCTAATT | TAGAAGATTT | GGTTGCGAAA | TCTAAAGAAA | TCGTAAGAGA | ATACGAAGGA | 1260 |
| AAACTTAATC | AATCTAAAAA | TCTTCCAGAA | TTAAAGCAAC | TAGAAGAGGA | AGCTCATTCG | 1320 |
| AAGTTGAAAC | AAGTTGTGGA | GGATTTTAGA | AAAAAATTTA | AACGTCAGA | GCAAGTGACA | 1380 |
| CCAAAAAAAC | GTGTCAAACG | AGATTTAGCT | GCTAATGAAA | ATAATCAACA | AAAGATTGAG | 1440 |
| TTAACAGTTT | CACCAGAGAA | TATCACTGTA | TATGAAGGTG | AAGACGTGAA | ATTTACAGTC | 1500 |
| ACAGCTAAAA | GTGATTCGAA | GACGACGTTG | GACTTCAGTG | ATCTTTTAAC | AAAATATAAT | 1560 |
| CCGTCTGTAT | CAGATAGAAT | TAGTACAAAT | TATAAGACTA | ACACGGATAA | TCATAAGATT | 1620 |
| GCCGAAATCA | CTATCAAGAA | TTTGAAGCTA | AATGAAAGTC | AAACAGTGAC | TCTAAAAGCT | 1680 |
| AAAGATGATT | CTGGCAATGT | AGTTGAAAAA | ACATTCACTA | TTACAGTGCA | AAAGAAAGAG | 1740 |
| GAGAAACAAG | CAAGAACCAA | AATCAAATGA | CAAGAATCAA | TTACAAGAGT | TGATTAAATC | 1800 |
| AGCTCAACAA | GAACTGGAAA | AGTTAGAAAA | AGCAATAAAA | GAATTAATGG | AGCAACCAGA | 1860 |
| GATTCCATCC | AATCCAGAGT | ATGGTATTCA | AAAATCTATT | TGGGAGTCAC | AAAAAGAGCC | 1920 |
| TATCCAGGAA | GCCATAACAA | GTTTTAAGAA | GATTATTGGT | GATTCATCTT | CAAAATACTA | 1980 |
| CACAGAGCAC | TATTTTAACA | AATATAAATC | TGATTTTATG | AATTATCAAC | TTCATGCACA | 2040 |
| AATGGAGATG | CTGACTAGAA | AAGTGGTTCA | GTATATGAAC | AAATATCCTG | ATAATGCAGA | 2100 |
| AATTAAAAAG | ATATTTGAGT | CAGATATGAA | GAGAACGAAA | GAAGATAATT | ACGGAAGTTT | 2160 |
| AGAAAATGAT | GCTTTGAAAG | GCTATTTTGA | GAAATATTTC | CTTACACCAT | TTAATAAAAT | 2220 |
| TAAGCAGATT | GTAGATGATT | TGGATAAAAA | AGTAGAACAA | GATCAGCCAG | CACCAATTCC | 2280 |
| GGAAAATTCA | GAAATGGATC | AGGCTAAGGA | AAAGGCTAAG | ATTGCTGTAT | CGAAGTATAT | 2340 |
| GAGTAAGGTT | TTAGATGGAG | TTCATCAACA | TCTGCAGAAG | AAAAATCACA | GTAAAATTGT | 2400 |
| TGATCTTTTT | AAGGAACTTG | AAGCGATTAA | ACAACAAACT | ATTTTTGATA | TTGACAATGC | 2460 |
| AAAGACTGAA | GTAGAGATTG | ATAACTTAGT | ACACGATGCA | TTCTCAAAAA | TGAATGCTAC | 2520 |
| TGTTGCTAAA | TTTCAAAAAG | GTCTAGAGAC | AAATACGCCA | GAAACTCCAG | ATACACCGAA | 2580 |
| GATTCCAGAG | CTACCTCAAG | CCCCAGATAC | ACCGCAGGCT | CCAGACACAC | CGCATGTTCC | 2640 |
| GGAATCACCA | AAGGCCCCAG | AAGCACCGCG | TGTTCCGGAA | TCACCAAAGA | CTCCAGAAGC | 2700 |
| ACCGCATGTT | CCGGAATCAC | CAAAGACTCC | AGAAGCACCA | AAGATTCCGG | AACCCCCTAA | 2760 |
| GACTCCAGAC | GTCCCTAAGC | TTCCAGACGT | CCCTAAGCTT | CCAGATGCAC | CGAAGTTACC | 2820 |
| AGATGGGTTA | AATAAAGTTG | GACAAGCAGT | ATTTACATCA | ACTGATGGAA | ATACTAAGGT | 2880 |
| TACGGTTGTA | TTTGATAAAC | CTACAGATGC | TGATAAGTTA | CATCTCAAGG | AAGTAACGAC | 2940 |
| GAAAGAGTTG | GCTGATAAAA | TTGCTCATAA | AACAGGAGGA | GGAACAGTTC | GTGTGTTTGA | 3000 |
| CTTATCTCTT | TCTAAAGGAG | GCAAGGAAAC | ACATGTCAAT | GGAGAACGAA | CTGTTCGGCT | 3060 |
| CGCGCTTGGG | CAGACTGGCT | CAGATGTTCA | CGTCTATCAC | GTAAAGGAAA | ATGGCGACCT | 3120 |
| TGAGCGTATT | CCTTCTAAAG | TTGAAAATGG | GCAAGTTGTT | TTTAAAACGA | ACCACTTCAG | 3180 |
| TTTGTTTGCG | ATTAAGACAC | TTTCTAAGGA | TCAAAATGTT | ACTCCACCGA | AGCAGACTAA | 3240 |
| ACCTTCTACC | CAAGGCAGTC | AAGTAGAGAT | TGCAGAGAGT | CAAACTGGAA | AATTCCAGAG | 3300 |
| TAAAGCAGCT | AATCATAAAG | CACTGGCTAC | TGGAAATGAA | ACAGTGGCAA | AAGGAAATCC | 3360 |
| TACATCAACA | ACGGAAAAGA | AATTGCCATA | TACAGGAGTG | GCATCTAATC | TAGTTCTTGA | 3420 |
| AATTATGGGT | CTCCTTGGTT | TGATTGGAAC | TTCATTCATC | GCAATGAAAA | GAAGAAAATC | 3480 |
| ATGATTCAGT | TTTTTAAAAA | TATCCACTTT | CGATATCTAG | CATTTGATTG | GTTATCTGTG | 3540 |

| | | | | | |
|---|---|---|---|---|---|
| GATGATTCTA | AAGATGTTAC | CTATCGTTGG | TATGTAACAA | TTATAAGTCA | TTTCATATAA | 3600 |
| AAGAGGCTCT | TTGTCAACTG | TAGTTGGTTG | AAACAACGTA | CAAACTAGAA | AGGACGCATT | 3660 |
| TTGTCCTTTC | TTTTGATGT | TGAGGGCAAT | GAAAATACGC | TTTTGAAGT | TTTCAAAATT | 3720 |
| CCGAAAACTA | | | | | | 3730 |